US012559761B2

(12) United States Patent
Arora et al.

(10) Patent No.: US 12,559,761 B2
(45) Date of Patent: Feb. 24, 2026

(54) RECOMBINANT EXPRESSION PLATFORM, CONSTRUCTS AND METHODS FOR EXPRESSION OF DIFFICULT TO EXPRESS PROTEINS (DTE-PS)

(71) Applicant: Premas Biotech Pvt Ltd, Gurgaon (IN)

(72) Inventors: Kajal Arora, Gurgaon (IN); Prabuddha Kumar Kundu, Gurgaon (IN); Ruchir Rastogi, Gurgaon (IN); Nupur Mehrotra Arora, Gurgaon (IN)

(73) Assignee: PREMAS BIOTECH PVT LTD, Gurgaon (IN)

( * ) Notice: Subject to any disclaimer, the term of this patent is extended or adjusted under 35 U.S.C. 154(b) by 827 days.

(21) Appl. No.: 17/878,657

(22) Filed: Aug. 1, 2022

(65) Prior Publication Data

US 2023/0097374 A1     Mar. 30, 2023

Related U.S. Application Data

(63) Continuation of application No. PCT/IN2021/050111, filed on Feb. 3, 2021.

(30) Foreign Application Priority Data

Feb. 3, 2020     (IN) ............................. 202011002479

(51) Int. Cl.
| | |
|---|---|
| *C12N 15/81* | (2006.01) |
| *C07K 14/005* | (2006.01) |
| *C07K 14/705* | (2006.01) |
| *C12N 9/00* | (2006.01) |
| *C12N 9/02* | (2006.01) |
| *C12N 9/10* | (2006.01) |
| *C12N 9/24* | (2006.01) |
| *C12P 21/02* | (2006.01) |

(52) U.S. Cl.
CPC ............ *C12N 15/81* (2013.01); *C07K 14/005* (2013.01); *C07K 14/705* (2013.01); *C07K 14/70596* (2013.01); *C12N 9/0071* (2013.01); *C12N 9/2402* (2013.01); *C12N 9/93* (2013.01); *C12Y 302/01018* (2013.01); *C12Y 602/01003* (2013.01); *C12N 2720/12352* (2013.01)

(58) Field of Classification Search
None
See application file for complete search history.

(56) References Cited

U.S. PATENT DOCUMENTS

| | | | |
|---|---|---|---|
| 5,268,290 A | 12/1993 | Hasegawa et al. | |
| 7,910,364 B2 | 3/2011 | Lima et al. | |
| 2004/0235095 A1 | 11/2004 | Denmeade et al. | |
| 2005/0191726 A1 | 9/2005 | Motwani et al. | |
| 2008/0076164 A1 | 3/2008 | Cirpus et al. | |

FOREIGN PATENT DOCUMENTS

| | | |
|---|---|---|
| CN | 1757745 A | 4/2006 |
| GB | 2249096 A | 4/1992 |
| WO | 1999036778 A1 | 7/1999 |
| WO | 2010134096 A2 | 11/2010 |
| WO | 20100134095 A2 | 11/2010 |
| WO | 2017035508 A1 | 3/2017 |

OTHER PUBLICATIONS

Greenberg, Harry, et al., "Serological Analysis of the Subgroup Protein of Rotavirus, Using Monoclonal Antibodies", Infection and Immunity, Jan. 1983, pp. 91-99, vol. 39, No. 1.
Hoshino, Yasutaka, et al, "Serotypic Similarity and Diversity of Rotaviruses of Mammalian and Avian Origin as Studied by Plaque-Reduction Neutralization", The Journal of Infectious Diseases, vol. 149, No. 5, May 1984, pp. 694-702.
Li, Bing, et al, "The effects of CD59 gene as a target gene on breast cancer cells", Cellular Immunology 272 (2011) pp. 61-70.
Lundstrom, Kenneth, et al, "Structural genomics on membrane proteins: comparison of more than 100 GPCRs in 3 expression systems", J Struct Funct Genomics (2006), pp. 77-91.
Massey-Gendel, Elizabeth, et al., "Genetic selection system for improving recombinant membrane protein expression in E. coli", Published online Dec. 15, 2008, Protein Science 2009, vol. 18, pp. 372-383.
Saccardo, Paolo, et al, "Tools to cope with difficult-to-express proteins", Published online: Apr. 14, 2016, pp. 1-9, Appl Microbiol Biotechnol.
Thoring, Lena, et al, "Accelerating the Production of Druggable Targets: Eukaryotic Cell-Free Systems Come into Focus", Published Apr. 16, 2019, pp. 1-21.
Thoring, Lena, et al., "High Yield production of "difficult-to-express" proteins in a continuous exchange cell-free system based on CHO cell lysates", Scientific Reports, Published online Sep. 15, 2017, pp. 1-15.

(Continued)

*Primary Examiner* — Manjunath N Rao
*Assistant Examiner* — Jae W Lee
(74) *Attorney, Agent, or Firm* — Brown Rudnick LLP; Adam M. Schoen

(57)     ABSTRACT

The present invention relates to expression of SARS-CoV like virus proteins [S, M and E] proteins; recombinant polynucleotides, polypeptides; constructs, virus-like particles (VLPs); immunogenic compositions or vaccines comprising Virus Like Particles (VLPs). Method of producing the VLPs/expressing the multi-subunit virus like proteins and method for co-expression of multi-subunit and virus like proteins (VLPs) are also provided. The present invention also provides strategies, methods, systems, kits and combinations for scalable expression, purification and enhanced production of the virus like proteins of SARS-CoV while maintaining their size range and composition. Such multi-subunit VLPs can be utilized to make immunogenic compositions or vaccines.

14 Claims, 9 Drawing Sheets

Specification includes a Sequence Listing.

(56)        References Cited

OTHER PUBLICATIONS

Zhang, Ronghua, et al,. "CD59: a promising target for tumor immunotherapy", Accepted for publication: Nov. 30, 2017; published online: Mar. 9, 2018, pp. 1-12.
International Search Report, PCT/IN2021/050111, Jul. 28, 2021, pp. 1-5.

| Samples | |
|---|---|
| BB 24hrs | Backbone control after 24hr induction |
| +tive conrl | His antibody positive control |
| BB-BI | Backbone control before induction |
| 6-24hr | Clone 6 after 24hr induction |
| 6-BI | Clone 6 before induction |
| 5-24hr | Clone 5 after 24hr induction |
| 5-12hr | Clone 5 after 12 hr induction |
| 5-BI | Clone 5 before induction |
| 6-12hr | Clone 6 after 12 hr induction |

Lane 1: Positive control
Lane 2: Marker
Lane 3: Protein 5 clone 13 Pellet
Lane 4: Protein 5 clone 13 Sup
Lane 5: Protein 5 clone 14 Pellet
Lane 6: Protein 5 clone 14 Sup
Lane 7: Backbone Lane 1: Protein 11 clone 24 Sup
Lane 2: Protein 11 clone 24 Pellet
Lane 3: Protein 11 clone 23 Sup
Lane 4: Protein 11 clone 23 Pellet
Lane 5: Backbone
Lane 6: Positive control
Lane 7: Marker

| Lane No. | Sample |
|---|---|
| 1 | Marker |
| 2 | Membrane preparation from Nav$_{1.7}$ overexpressing cell |
| 3 | Membrane preparation from vector control cells |

RECOMBINANT EXPRESSION PLATFORM, CONSTRUCTS AND METHODS FOR EXPRESSION OF DIFFICULT TO EXPRESS PROTEINS (DTE-PS)

RELATED APPLICATIONS

The present application is a continuation of international application PCT/IN2021/050111 filed Feb. 3, 2021, which claims the benefit of Indian Patent Application number 202011002479 filed Feb. 3, 2020, each of which is hereby incorporated by reference in its entirety.

TECHNICAL FIELD

The present invention broadly lies in the field of recombinant protein expression. More particularly, the present invention relates to expression of difficult to express proteins in a recombinant expression platform; constructs, methods and kits involved in expressing such DTE-Ps through the said system.

BACKGROUND OF THE ART

Successful recombinant expression of proteins is a key requirement of the biotech industry to aid in drug discovery and in the production of bio-therapeutics and vaccines. This entails not only successful expression but also high quality and large-scale production of the target proteins. Host cells such as *E. coli*, yeast, mammalian and insect cell-based expression systems are generally selected to achieve successful expression of well-folded and active form of such proteins in recombinant mode. However, there are numerous proteins which do not express efficiently due to their inherent nature such as hydrophobicity, higher cysteine-proline residues, repetitive amino acids, protein half-life, mRNA turnover, stable RNA production etc. Suitability of host cells also plays an important role in achieving the desired expression. Hence, a robust and consistent platform and host system is required for expression of such proteins along with commercial scalability and cost-effective production for supply in the industry in required amounts and cost.

Many proteins which are important for various applications are categorized under difficult to express category and may pose a challenge in expression and manufacturing of these proteins for industrial scale production. This could be ascribed to lower or no expression due to sequence complexities or problems like, manufacturing scale ups, product recovery or purification. Further, applying varied host systems and methodologies and cumbersome optimizations, make it a very unpredictable, laborious, costly and time-consuming affair.

Expression of few challenging proteins using various vectors and hosts, is reported in the prior art. Indian patent application numbers 1017/DEL/2009 and 1018/DEL/2009, disclose heterologous over-expression of one such protein, i.e., human cytochrome P450 reductase. However, these documents focus on the expression of cytochrome P450 specifically with a different construct.

Another patent document CN1757745A relates to a method of high efficiency expression of exogenic protein using methanol yeast system.

U.S. Pat. No. 7,910,364B2 discloses rapidly cleavable sumo fusion protein expression system for difficult to express proteins.

Saccardo et al., 2016 have shed some light on the general techniques and tools to cope with expression of difficult to express proteins.

Thoring et al., 2017 reported high-yield production of difficult to express proteins in a continuous exchange cell-free system based on CHO cell lysates.

However still, there are a large number of difficult to express proteins which remain a challenge for researchers globally. Additionally, not many successes have been achieved in the aspect of commercial scalability for over-expression and purification with enhanced quality and scalable amount. Furthermore, there is a big lacuna in the art to have a stable, consistent and robust platform for expression of difficult to express recombinant proteins across varied origin and families, with scalability as well as quality of expressed target protein.

For instance, more than 50% of known and novel drug target receptors and vaccine targets are recognized as membrane proteins. It is also well understood that over-expression of membrane proteins in their full length including all the domains is not an easy task. Recombinant expression of proteins with transmembrane domain/s in heterologous systems is also very challenging due to their high hydrophobic nature and sequence complexities which lead to aggregation, precipitation, incorrect protein folding of proteins are difficult to solubilize and refold (Lundstrom et al. 2006). These proteins are usually expressed as modified proteins with deletion of the transmembrane domain, using *E. coli* host system to avoid insoluble expression. The drawback with this approach is that this results in lack of full-length sequence expression and consequently, a lack of full-length protein for analysis. Eukaryotic host systems are recommended for their expression in their natural form, as intact and full-length for their biochemical and structural characterization requirements. As per available literature, there are no universal solutions for membrane protein production, and this continues to remain a considerable obstacle (Elizabeth Massey-Gendel et al. 2009).

Expressing nascent polypeptide chain and intimate interactions and insertion in membrane is one important parameter to study a particular protein with respect to its analysis as drug target or vaccine candidate.

There is a need in the art for providing a stable and versatile expression system for expressing multiple full-length transmembrane proteins. As an example, the inventors have demonstrated the expression of full-length and functionally active Neuraminidase (NA), a transmembrane DTE-P. Other than the difficulty of expressing Neuraminidase as membrane anchored protein, its sequence is also found to have high number cysteine residues and hydrophobicity which further describes its tendency towards insoluble expression and aggregation in expression systems like *E. coli*. The presence of high proline residues also adds instability being helix breaker for stable product generation. Limited literature for recombinant expression of full-length NA expression is available in yeast host expression system. Currently there is an unmet need to develop a universal effective vaccine which elicits immune response against influenza virus and subtypes. Full length NA expression is of utmost importance to analyse the immune response including conformation epitopes. To perform such functions, it is required to express neuraminidase efficiently.

Similarly, expression of structural proteins, which are considered difficult to express, do not emerge in fully soluble, well-folded, and active form in a heterologous expression system. Their major characteristic is the tendency to aggregate and form inclusion bodies. Viral surface glycoproteins and other capsid proteins, which belong to the family of structural proteins, have been long recognized as functional targets for vaccines. Vaccine candidates like capsid protein could be an attractive strategy to induce protection against severe viral diseases.

The versatile platform described in this application is able to express some of the difficult to express structural proteins. The inventors have demonstrated, that the claimed platform allows for the stable and enhanced expression of capsid glycoprotein viral protein VP7 which is a 347 amino acids long glycosylated protein with added His-tag. The sequence contains high number of cysteine and proline residues along with high hydrophobicity and is hence a difficult to express protein. The features describe that the protein has tendency towards insoluble expression and aggregation when over-expressed, which recommends its expression using a eukaryote system. Additionally, high number of proline residues, which is a structure breaker, puts the protein in unstable category. The neutralizing antibodies against the protein may provide both serotype specific and cross-reac-tive protection and hence considered important for vaccine development in human healthcare stream.

The inventors have also demonstrated that the platform of the present invention is capable of expressing enzyme proteins, such as fatty acid enzymes. Few fatty acids and derivatives known as polyunsaturated fatty acids (PUFA) are very essential and have functions including inflammatory response, controlling lipid metabolism and also have func-tion in signaling pathways (Hoshino et al., 1984). Desatu-rase enzymes, a key representative of such fatty acid enzymes, are transmembrane proteins varying from being single pass to multi-pass and likely to be localized in endoplasmic reticular membranes of plants, fungi and ani-mals.

Progress on the study of desaturases has been constrained due to the complexity in membrane protein extraction and crystallization of these enzymes. Consequently, the knowl-edge about the structure and expression regulation of mem-brane-bound fatty acid desaturases is still lacking and whether the transmembrane domain has any role in fatty acid desaturase efficiency remains unknown (Wyatt et al., 1983). Destaurases have high hydrophobicity as described by its membrane nature, high cysteine and proline content. The attributes keep it in difficult to express category and describes tendency for insoluble expression if expressed in bacterial host system. Hence, it is of utmost importance to have dependable and efficient systems to express these difficult to express enzyme proteins, especially for produc-ing them on a commercial scale. The inventors have suc-cessfully demonstrated the expression of 4-multi-pass mem-brane protein sequences of desaturase through the platform of the present invention.

Further, fatty acid elongation is also a very crucial step, serving as an alternative pathway of fatty acid production involved in lipid metabolism applications. Elongase proteins also have high hydrophobicity, high cysteine and proline content. These attributes make them difficult to express. Besides, there is a tendency for insoluble expression if expressed in bacterial host system.

Many important proteins, such as ion pumps, ion chan-nels, and transporters, span the membrane multiple times. Each membrane-spanning α helix in these multi-pass trans-membrane proteins is thought to act as a topogenic sequence. In nature, transmembrane proteins mediate com-munication between cells, ferry molecules into and out of the cell, and are common targets for drugs. Expression of nascent polypeptide chain and intimate interactions and insertion in membrane is one important parameter to study a particular protein with respect to its analysis as drug target or vaccine candidate. However, predicting how a large, multi-pass transmembrane protein design might fold into shape and function while spanning such different environ-ments has been challenging.

Recombinant expression of proteins with transmembrane domain/s in heterologous systems is also very challenging due to their high hydrophobic nature and sequence com-plexities which leads to aggregation, precipitation, and incorrect protein folding of proteins and are difficult to solubilize and refold. To produce well-ordered multi-pass transmembrane proteins from scratch, several biophysical demands have to be balanced at the same time. Placing hydrophobic swatches on alpha-helical structures is suffi-cient to generate membrane-association, but the packing and orientation of hydrophobic helices are difficult to control. Thereby expression of such multi transmembrane proteins in prokaryotes and then refolding them to generate them in correct conformation is not an easy task.

The inventors have successfully demonstrated the expres-sion of an ion channel receptor, a multi-pass membrane protein Nav1.7 through the versatile platform of the present invention. Nav1.7 is a voltage-gated sodium channel medi-ates the voltage-dependent sodium ion permeability of excit-able membranes and implicated in pain signaling. Nav1.7 is a validated and promising drug target for pain treatment in humans.

Nav1.7 is glycosylated 1988 amino acids long, multi-pass membrane protein with 24 trans membrane domains and is localized to cell/plasma membrane. The principal subunit of this channel is a protein of >200 kDa, the alpha subunit. The sequence contains 4 internal repeats, each with 5 hydropho-bic segments (S1, S2, S3, S5, S6) and one positively charged segment (S4).

The protein contain oligomeric conformation, very big in size, high and odd number of cysteines, proline residues and high hydrophobicity. Observed parameter shows the over expression of protein may yield in-soluble expression and aggregation in prokaryotes. Both high size and prolines residues (a helix breaker) further can lead to degradation. The instability index of this protein classifies this protein as unstable protein.

In some culture models, it was found that the receptor expression degrades or dysregulates, creating difficulty in expression of Nav1.7 over time in culture. Inventors of the present invention have successfully demonstrated the expression of the full-length membrane-anchored alpha sub-unit of Nav1.7 by the recombinant expression platform of the present invention.

Another important category of the DTE-Ps are drug target molecules (GPI anchored protein). Major drug target classes belong to antineoplastics, G protein-coupled receptors (GPCR's), ion channels, kinases and proteases (Kubic et al, 2019). A broad range of protein expression systems are currently available, mostly based on cellular organisms of prokaryotic and eukaryotic origin. Limitations of prokary-otic systems occur when complex mammalian target pro-teins requiring posttranslational modifications, cofactors and chaperones for correct protein folding, assembly and activity need to be produced.

One such drug target protein is CD59 protein which is a glycosylphosphatidylinositol-anchored (GPI anchored) membrane protein that acts as an inhibitor of the formation of the membrane attack complex to regulate complement activation. Recent studies have shown that CD59 is highly expressed in several cancer cell lines and tumor tissues.

CD59 also regulates the function, infiltration, and phenotypes of a variety of immune cells in the tumor microenvironment. (Zhao et al, 2018). CD59 is being considered as a promising target in the gene therapy of breast cancer. (Xu et al).

To circumvent these issues, eukaryotic cell-based expression systems, including yeast systems (*Pichia pastoris, Saccharomyces cerevisiae, Kluyveromyces lactis*) and mammalian systems (HEK293, Chinese hamster ovary cells (CHO cells)), have been proposed in the art. Mammalian systems are only rarely reported as being successful. Generation of eukaryotic stable cell lines for protein production purposes have been found to be quite laborious due to slow cell growth, and low protein yields apart from high production time thereby leading to costly protein production processes. (Kubic et al, 2019).

As discussed in the preceding paragraphs, it is a need of the hour to have an efficient recombinant expression system/platform which is flexible and adaptable for the expression and production of varied DTE-Ps. The desirable features demand optimum expression, quick and time saving standardized methodologies and scalability ease with capability of producing large amount of material for analysis, diagnostic and therapeutic use amenable to cater the large population with cost effectiveness.

Hence, the present invention addresses this need by presenting a versatile recombinant protein expression platform comprising recombinant expression vectors with protease deficient yeast cell host system capable of expressing the target DTE-P proteins from varied origin and families, at a scalable and commercial level. The claimed recombinant expression platform and methods overcome the shortcomings of the prior arts and provide significant technical advance over the same.

OBJECTIVES OF THE INVENTION

The principal objective of the present invention is to provide a versatile yeast-based recombinant expression platform for the enhanced expression of full length or truncated target "Difficult to Express" proteins (DTE-Ps) of diverse origin and families.

Yet another objective of the present invention is to provide a method for the enhanced expression of DTE-Ps using the recombinant expression platform of the present invention.

Yet another objective of the present invention is to provide a kit comprising the recombinant expression platform of the present invention for producing the target DTE-Ps.

Another important objective of the present invention is to provide a versatile recombinant yeast-based platform, method and kit for enhanced expression and scalability of the desired DTE-Ps with all their functions intact.

BRIEF DESCRIPTION OF FIGURES AND DRAWINGS

The accompanying drawings illustrate some of the embodiments of the present invention and, together with the description, explain the invention. These drawings have been provided by way of illustration and not by way of limitation.

Figure 10:
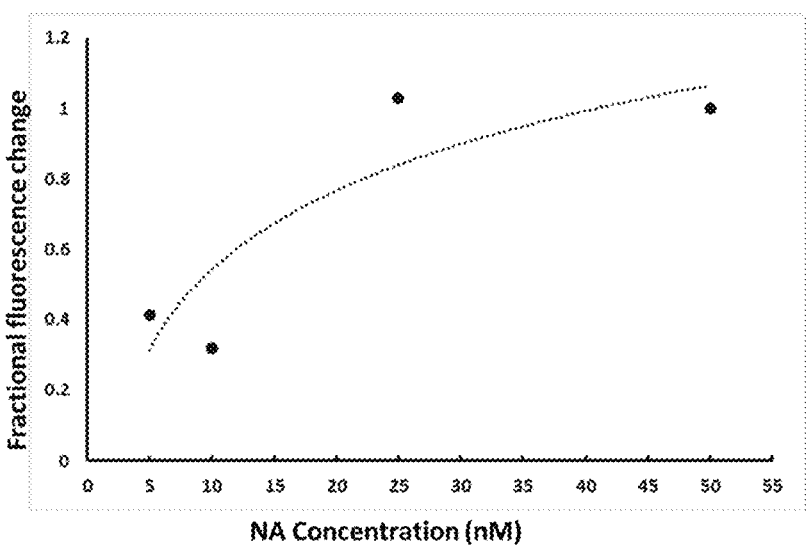

FIG. 10 Activity assay of Neuraminidase

Figure 11:
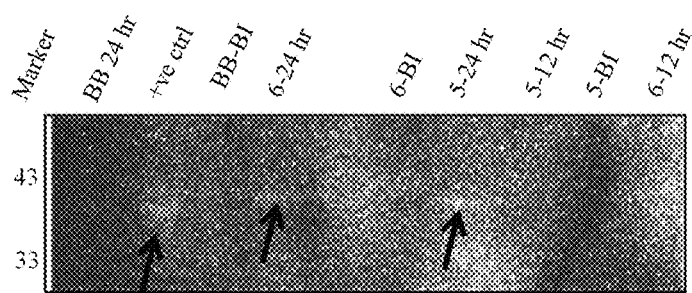

FIG. 11 shows Immunoblot analysis of expression of VP7.

Figure 12:
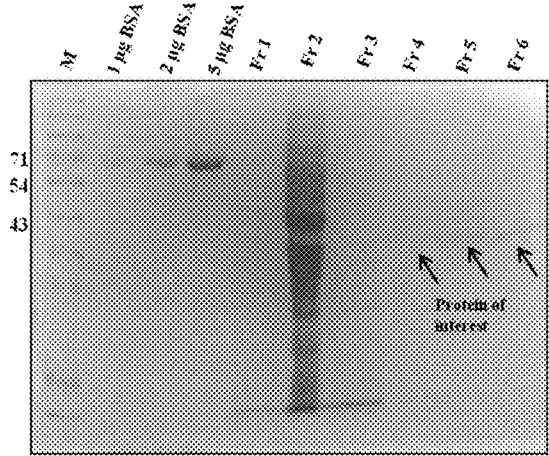

FIG. 12 shows SDS PAGE analysis of purified VP7 protein.

Figure 13:
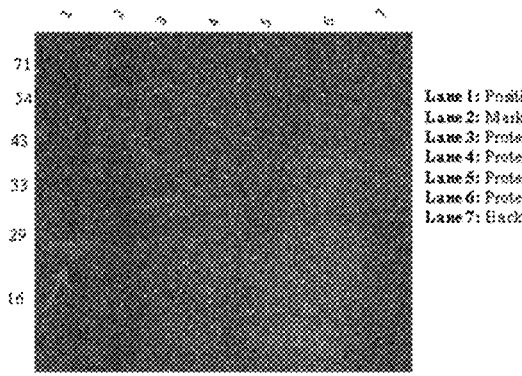

FIG. 13 shows Immunoblot analysis confirming expression of fatty acid desaturase protein.

Figure 14:
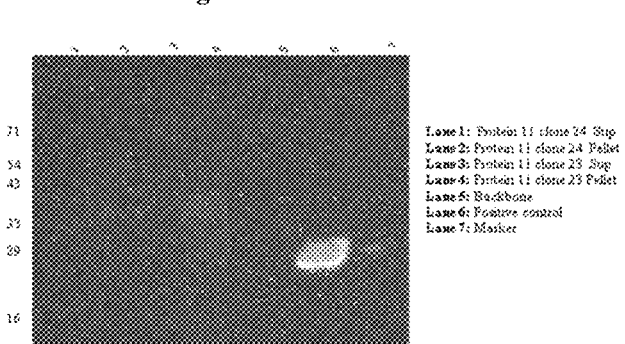

FIG. 14 shows Immunoblot analysis confirming the expression of fatty acid elongase protein.

Figure 15:
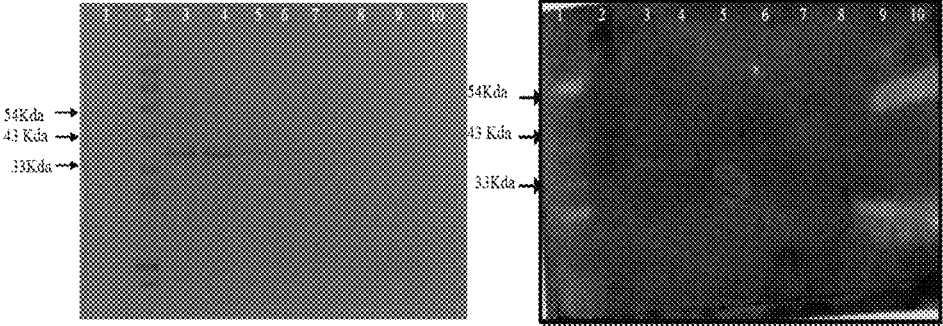

FIG. 15 illustrates SDS PAGE and Immunoblot analysis of purified fatty acid elongase protein from scale up culture.

Figure 16:
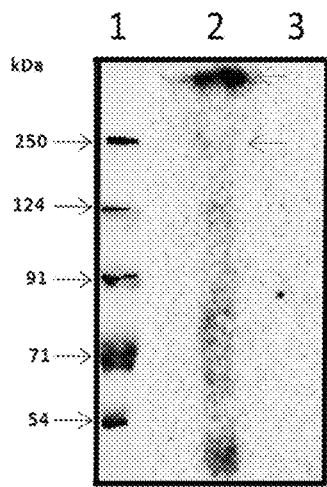

FIG. 16 depicts Immunoblot analysis showing expression of Nav1.7.

Figure 17:
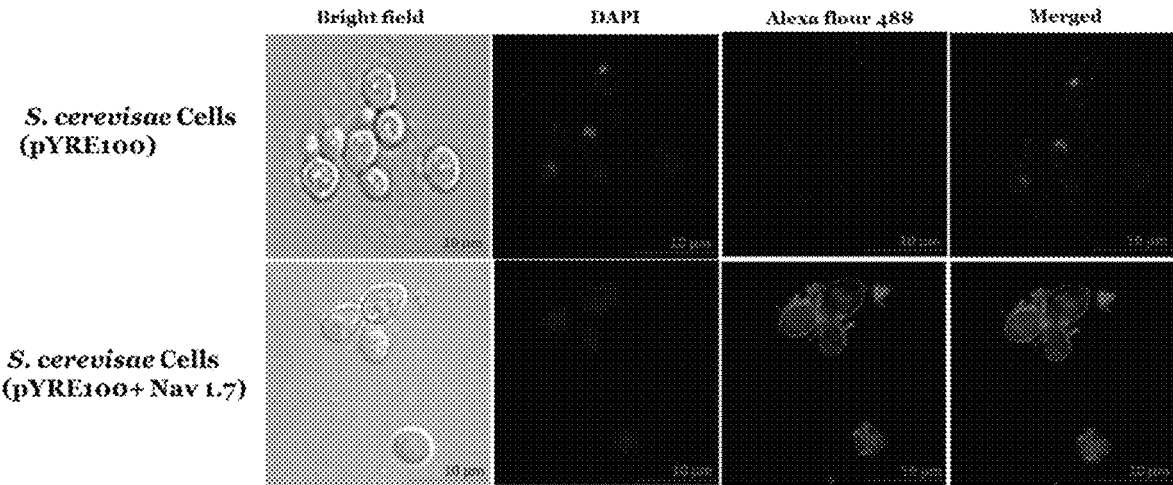

FIG. 17 illustrates Confocal Microscopy showing surface expression of NaV1.7.

Figure 18:
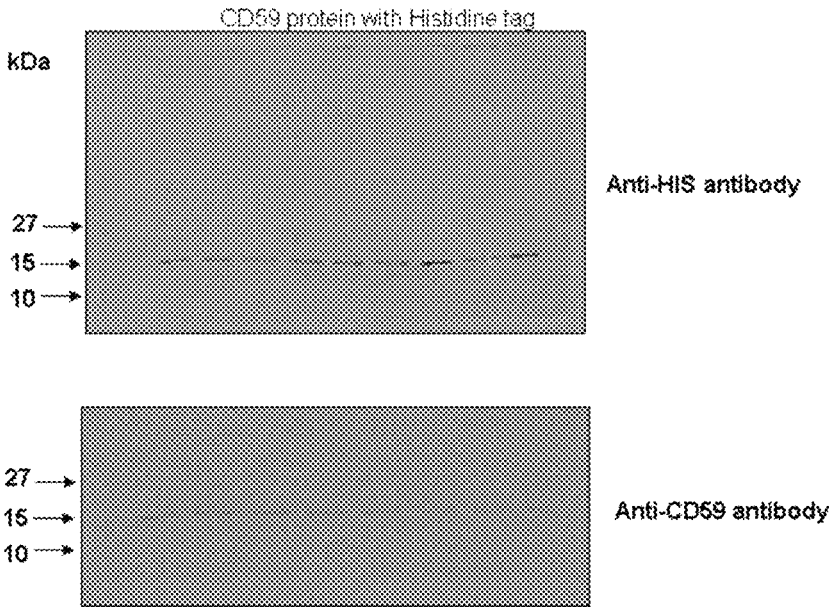

FIG. 18 shows the Immunoblot analysis using Anti-His antibody and Anti-CD59 antibody to confirm overexpression of CD59 protein.

Figure 19:
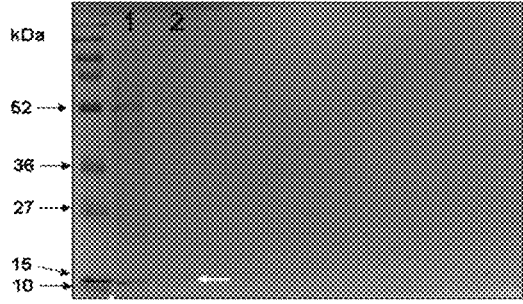

FIG. 19 shows the purification of CD59 protein.

SUMMARY

The present invention relates to the expression of difficult to express proteins (DTE-Ps) in a recombinant expression platform and discloses a versatile recombinant expression platform comprising:

i. an array of yeast based expression vectors, wherein the vectors are selected from one or more episomal or integrated yeast-based expression vectors operably linked with promoters selected from Gal1 promoter, ADH2 promoter or Gal10 promoter; wherein the promoters can be used singly or in combination; the said vector comprising an auxotrophic selection marker selected from Leu or Ura3, CYCT1 terminator; resistance marker Ampicillin; pUC ori; 2 micron origin; a specific upstream regulatory sequence and a sequence region comprising of multiple cloning sites, wherein desired target proteins could be incorporated; wherein the said vector directs insertion of full length or truncated polynucleotide sequence encoding the desired target protein into the host cell;

ii. engineered protease deficient yeast host cell with disrupted endogenous genes encoding PRB1, PEP4, uracil, lysine, adenine and leucine auxotrophic markers and wherein said platform allows for enhanced expression of difficult to express proteins of diverse origin and families.

Constructs, methods and kits involved in expressing such DTE-Ps through the said system are also described.

DETAILED DESCRIPTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

Definitions

The use of "comprise", "comprises", "comprising", "contain", "contains", "containing", "include", "includes", and "including" are not intended to be limiting. It is to be understood that both the foregoing general description and this detailed description are exemplary and explanatory only and are not restrictive.

The term "difficult-to-express proteins (DTEPs)" defines the proteins that are difficult to or impossible to emerge in fully soluble, well-folded, and active form in a heterologous expression system.

The term "expression platform" defines a system to produce large amounts of proteins, sugars or other compounds for research or industrial uses.

The term "expression vectors" defines a plasmid or virus designed for gene expression in cells.

The term "host cell" means a host cell used for generation of recombinant proteins.

The term "prokaryotic proteins" includes the proteins found in prokaryotic cells/organisms.

The term "eukaryotic proteins" includes the proteins found in eukaryotic cells/organisms.

The term "viral proteins" includes proteins generated by viruses including enzyme proteins as well as structural proteins such as capsid and viral envelope.

The term "mammalian proteins" include proteins produced in mammals.

The term "plant protein" includes proteins produced in plants.

The term "algal proteins" include the proteins found in all class of algae.

The term "highly hydrophobic proteins" includes proteins with side chains that do not like to reside in an aqueous environment and hence difficult to express and purify.

The term "proteins with multiple transmembrane" includes proteins predominantly with nonpolar amino acid residues with possibility of traversing the bilayer once or several times.

The term "transmembrane proteins" includes type of integral membrane proteins that span the entirety of the cell membrane.

The term "structural proteins" includes the proteins that have typical amino acid sequence which are repetitive and contributes to the framework and provides mechanical strength to the living organism or cell.

The term "ion channel receptors" includes multimeric proteins usually located in the plasma membrane.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art.

The present invention discloses recombinant yeast-based expression platform, for enhanced expression of difficult to express proteins (DTE-Ps) of various families and origin.

The disclosed platform uses a recombinant yeast host-based system. The platform includes the array of vectors, both integrative and episomal, with designed upstream regulatory sequence; engineered protease deficient yeast host (Protease deficient strain) and codon harmonization for the robust and enhanced expression of sequence optimized proteins from different origin and families. Multiple engineered expression strains can be selected depending on target protein and its intrinsic properties.

The present invention further discloses the use of single recombinant expression platform for expression of several target proteins, including DTE-Ps of plant, human, animal, bacterial, fungal or viral origin, and with various levels of complexity, different sources, categories and families.

In the principal embodiment, the present invention provides a versatile recombinant expression platform comprising:

i. an array of one or more episomal or integrated yeast based expression vectors operably linked with one or more promoters selected from Gal1 promoter, ADH2 promoter or Gal10 promoter; wherein the promoters can be used singly or in combination; the said vector comprising an auxotrophic selection marker selected from Ura3 or Leu; a terminator CYCT1; an Ampicillin resistance marker; an origin of replication site pUC ori; a 2 micron origin; one or more specific upstream regulatory sequences and a sequence region comprising of multiple cloning sites; wherein said vector directs insertion of full length or truncated polynucleotide sequence for desired target proteins into the host cell;

ii. engineered protease deficient yeast host cell with disrupted endogenous genes encoding protease PRB1, protease PEP4 and auxotrophic markers uracil, lysine, adenine and leucine; and wherein said platform allows for enhanced expression of difficult to express proteins of diverse origin and families.

In still another embodiment, engineered protease deficient yeast host cell with disrupted endogenous genes encoding protease PRB1, protease PEP4 and auxotrophic markers uracil, lysine, adenine and leucine is of *Saccharomyces cerevisiae* origin.

In yet another embodiment, said difficult to express proteins are from diverse origin and families and are selected from, but not limited to, viral, prokaryotic, eukaryotic, mammalian, human, plant, virus family, algal proteins, toxins, highly hydrophobic proteins, proteins with multiple transmembrane domains, transmembrane proteins, structural proteins, non-structural proteins, drug target receptors such as ion channel family, G-protein coupled receptors (GPCRs), GPI anchored proteins, enzymes, TNFR family, plasma membrane and those found in endoplasmic reticulum, Golgi compartment and cytosol localized proteins In still another embodiment, said difficult to express protein is a viral protein and the said viral protein could be a viral enzyme protein and in turn the said viral enzyme protein could be a membrane bound single pass membrane protein, such as a Neuraminidase.

In still another embodiment, the present invention proposes a nucleic acid construct with SEQ ID NO 7 for expression of membrane bound Neuraminidase wherein said construct comprises a nucleic acid sequence with SEQ ID NO 1 encoding for full length Neuraminidase, and an episomal expression vector comprising Ura3 auxotrophic selection marker, CYCT1 terminator, an Ampicillin resistance marker, pUC ori along with Gal1 promoter.

In still another embodiment, the present invention discloses a method of producing membrane bound Neuraminidase by the recombinant expression platform, comprising the steps of:

i. preparing the nucleic acid construct;

ii. transforming the said construct in protease deficient yeast host cell;

iii. culturing the transformed host cell for enhanced expression of Neuraminidase.

In yet another embodiment, said Neuraminidase protein elicits an immunogenic response and is functionally active.

In still another embodiment, said difficult to express protein could be a highly hydrophobic viral protein, the said highly hydrophobic viral protein being a structural protein, which could be a capsid protein, such as VP7. The said highly hydrophobic viral structural, capsid protein VP 7 being a vaccine candidate.

In yet another embodiment, the present invention discloses a nucleic acid construct with SEQ ID No 8 for expression of viral structural capsid protein VP7, wherein said construct comprises a nucleic acid sequence SEQ ID NO 2 encoding for full length VP7, and an episomal expression vector comprising Ura3 auxotrophic selection marker, CYCT1 terminator, an Ampicillin resistance marker, pUC ori along with Gal1 promoter.

In yet another embodiment, the present invention proposes a method of producing highly hydrophobic viral structural capsid protein VP7 by the recombinant expression platform, comprising the steps of:

i) preparing the nucleic acid construct;

ii) transforming the said construct in protease deficient yeast host cell;

iii) culturing the transformed host cell for enhanced expression of VP7.

In still another embodiment, said difficult to express protein could be a multi-pass transmembrane protein, said multi-pass transmembrane protein being from ion channel receptor family and such multi-pass transmembrane protein is from ion channel receptor family and the said protein can be a Nav 1.7 protein and the same could be a drug target receptor protein.

In yet another embodiment, A nucleic acid construct with SEQ ID NO 9 for expression of transmembrane ion channel receptor protein Nav1.7, wherein said construct comprising a nucleic acid sequence SEQ ID NO 3 encoding for full length Nav1.7, and an episomal expression vector comprising Ura3 auxotrophic selection marker, CYCT1 terminator, an Ampicillin resistance marker, pUC ori along with Gal1 promoter.

In yet another embodiment, the present invention proposes a method of producing transmembrane Nav1.7 protein by the recombinant expression platform of the present invention comprising the steps of:

i) preparing the nucleic acid construct;

ii) transforming the said construct in protease deficient yeast host cell;

iii) culturing the transformed host cell for enhanced expression of Nav1.7.

iv) surface localization of expressed Nav1.7 using confocal microscopy.

In still another embodiment, said difficult to express protein could be an enzyme protein which being a transmembrane protein. Such transmembrane protein is from lipid biosynthesis cycle and being a fatty acid desaturase and can be from fungal origin.

In yet another embodiment, the present invention proposes a nucleic acid construct with SEQ ID NO 10 for expression of fatty acid desaturase, wherein said construct comprising a nucleic acid sequence SEQ ID NO 4 encoding for full length Nav1.7, and an episomal expression vector comprising Ura3 auxotrophic selection marker, CYCT1 terminator, an Ampicillin resistance marker, pUC ori along with Gal1 promoter.

In still another embodiment, the present invention proposes a method of producing fatty acid desaturase protein by the recombinant expression platform comprising the steps of:

i) preparing the nucleic acid construct;

ii) transforming the said construct in protease deficient yeast host cell;

iii) culturing the transformed host cell for enhanced expression of fatty acid desaturase.

In still another embodiment, said difficult to express protein is an enzyme protein and being a transmembrane protein from lipid biosynthesis cycle. Said transmembrane protein from lipid biosynthesis being a fatty acid elongase.

In still another embodiment, the present invention proposes a nucleic acid construct with SEQ ID NO 11 for expression of fatty acid elongase, wherein said construct comprising a nucleic acid sequence with SEQ ID NO 5 encoding for full length elongase, and an episomal expression vector comprising Ura3 auxotrophic selection marker, CYCT1 terminator, an Ampicillin resistance marker, pUC ori along with Gal1 promoter In yet another embodiment, the present invention discloses a method of producing fatty acid elongase protein by the recombinant expression platform, comprising the steps of:

i) preparing the nucleic acid construct;

ii) transforming the said construct in protease deficient yeast host cell; culturing the transformed host cell for enhanced expression of fatty acid elongase.

In still another embodiment, said difficult to express protein could be a glycosylphosphatidylinositol-anchored (GPI anchor) protein and could be a drug target protein, the said drug target protein being CD59 of human origin.

In yet another embodiment, the present invention proposes a nucleic acid construct with SEQ ID NO 12 for expression of GPI anchor protein CD59, wherein said construct comprising a nucleic acid sequence with SEQ ID NO 6 encoding for full length elongase, and an episomal expression vector comprising Ura3 auxotrophic selection marker, CYCT1 terminator, an Ampicillin resistance marker, pUC ori along with Gal1 promoter.

In still another embodiment, the present invention proposes a method of producing GPI anchor CD59 protein by the recombinant expression platform comprising the steps of:

i) preparing the nucleic acid construct;

ii) transforming the said construct in protease deficient yeast host cell;

iii) culturing the transformed host cell for enhanced expression of CD59.

In still another embodiment, said platform is scalable and capable of producing proteins from diverse origin and families at an industrial scale.

In yet another embodiment, the present invention provided a kit comprising the recombinant expression platform comprising:

i) nucleic acid constructs encoding for said difficult to express target proteins;

ii) engineered protease deficient yeast host cells;

iii) instruction manual for operating said kit.

TABLE 1

SEQ IDs corresponding certain target proteins and respective constructs

| SEQ IDs | Target proteins/respective constructs |
|---|---|
| SEQ ID NO 1 | Neuraminidase |
| SEQ ID NO 2 | VP7 |
| SEQ ID NO 3 | Nav1.7 |
| SEQ ID NO 4 | Desaturase |
| SEQ ID NO 5 | Elongase |
| SEQ ID NO 6 | CD59 |
| SEQ ID NO 7 | Neuraminidase vector construct |
| SEQ ID NO 8 | VP7 vector construct |
| SEQ ID NO 9 | Nav1.7 vector construct |
| SEQ ID NO 10 | Desaturase vector construct |
| SEQ ID NO 11 | Elongase vector construct |
| SEQ ID NO 12 | CD59 vector construct |

Representative *S. cerevisiae* expression vectors as developed and used in the present invention are designated as below:

a. pYRI100 yeast integrative vector comprising Leu auxotrophic selection marker, CYCT1 terminator, resistance marker, pUC ori along with Gal promoter.

b. pYRI200 yeast integrative vector comprising Leu auxotrophic selection marker, CYCT1 terminator, resistance marker, pUC ori along with ADH2 promoter.

c. pYRE100 yeast episomal vector comprises Ura3 auxotrophic selection marker, CYCT1 terminator, resistance marker for selection, pUC ori along with Gal promoter.

d. pYRE200 yeast episomal vector comprises Ura3 auxotrophic selection marker, CYCT1 terminator, resistance marker for selection, pUC ori along with ADH2 promoter.

The sequence listing material in computer readable form xml file (66 kilobytes) created Oct. 12, 2022 entitled "31014-011_Sequence_Listing_08012022", containing sequence listing numbers 1-12, has been electronically filed herewith and is incorporated by reference herein in its entirety.

EXAMPLES

The present invention is further described hereinbelow by way of illustration and more particularly, the following paragraphs are provided in order to describe the best mode of working the invention and nothing in this section should be taken as a limitation of the claims.

Example 1: Expression of Neuraminidase (NA)

The present example uses Influenza A virus (A/Hatay/2004/(H5N1) as study example for expression using recombinant expression platform. Variant was also expressed successfully using same methodologies showing the platform adaptability, time saving and cost-effective approach. Full length Amino acid sequence of NA (449aa) was utilized.

Example 1.2: Cloning and Construct Preparation

Figure 1:
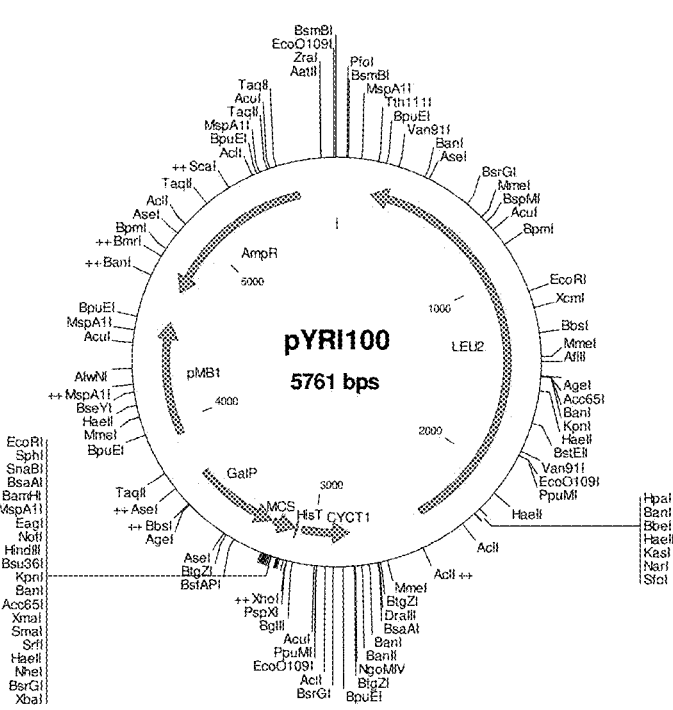
FIG. 1 shows the pYRI100 yeast integrative vector for expression of recombinant proteins using inducible GAL promoter.
Figure 2:
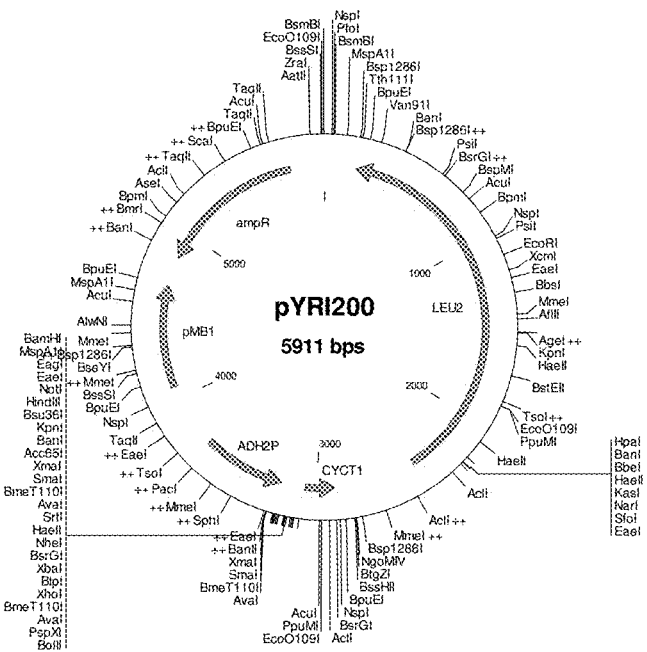
FIG. 2 shows the pYRI200 yeast integrative vector for expression of recombinant proteins using ADH2 constitutive promoter.
Figure 3:
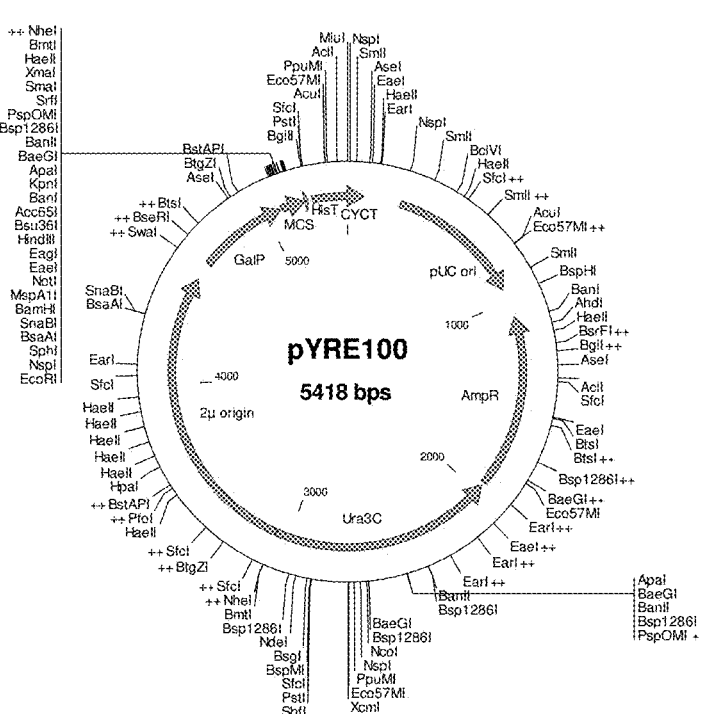
FIG. 3 shows pYRE100 yeast episomal vector for expression of recombinant proteins using inducible GAL promoter.
Figure 4:
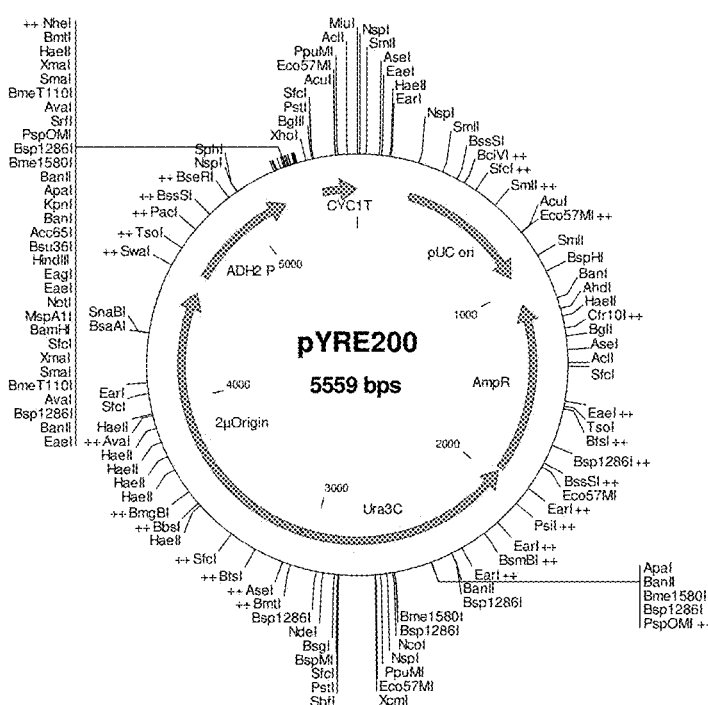
FIG. 4 shows pYRE200 yeast episomal vector for expression of recombinant proteins using ADH2 constitutive promoter.
Figure 5:
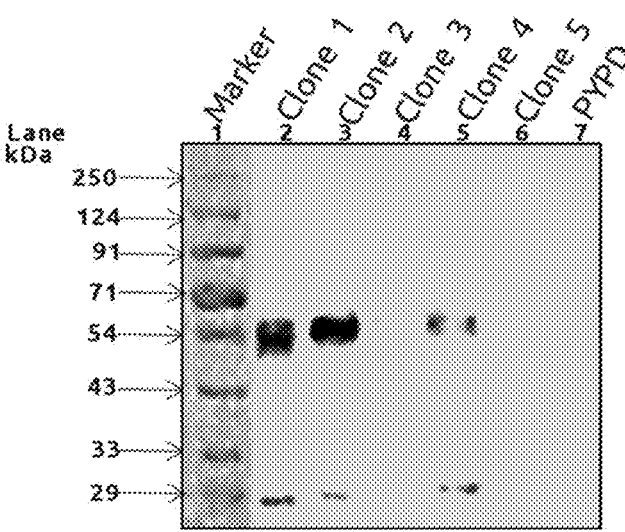
FIG. 5 shows Western Blot analysis of Neuraminidase.

The gene was cloned using conventional cloning methodologies into expression plasmid pYRE100 (FIG. 3) such that the expression protein has a C-terminus His tag. The cloned gene was analyzed through restriction digestion. The construct was transformed into *S. cerevisiae* host of recombinant expression platform for expression studies using anti-His antibody immunoblots analysis (FIG. 5).

Example 1.2: Transformation in *S. cerevisiae* Protease Deficient Host Strain The characterized recombinant construct was finalized for expression studies. The construct was transformed into protease deficient yeast strain using Lithium acetate/SS-DNA/PEG mediated protocol and transformants were selected over YNB Glucose—URA plates along with control (Protease deficient strain transformed with pYRE100 vector backbone). Few isolated healthy transformed colonies were inoculated in 10 ml of YNB Glucose—URA media and were analyzed for expression in $24^{th}$ hr post induced (Induction at late log phase $^A600$~5.0 OD/ml; final concentration 2% galactose) time point samples using anti-His antibody by Immuno-blot analysis Immuno Blot analysis using anti His antibody showed a specific band at higher size of ~52 kda due to glycosylation of the protein in three colonies (Lane 2, 3 and 5) of induced cultures. However, no band was observed in control sample (FIG. 5).

Figure 6:
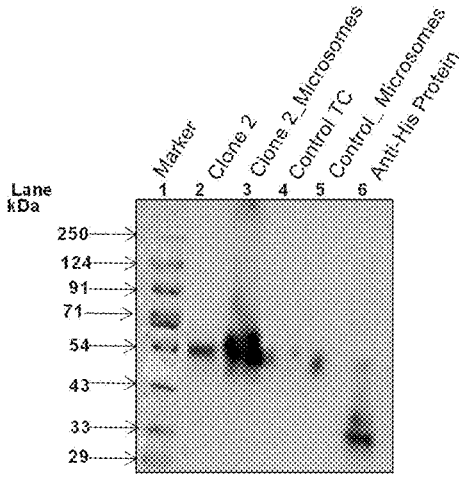
FIG. 6 shows the Western Blot analysis of Neuraminidase at large scale.

Results:

The *S. cerevisiae* strain and vector combination disclosed herein is used to express a significant viral vaccine candidate like Neuraminidase. The expressed protein was also found to be membrane anchored as it purified in the microsomal preparations. The current study demonstrates robustness of the developed expression platform as NA has mostly been expressed without the membrane anchor domain Thus, the expressed platform can be scaled up to develop a robust expression system for large scale production of viral vaccine candidates. The clone was further scaled up to 100× of volumetric scale. From the membrane fraction; microsomes were prepared using protocol mentioned in example. Expression was analysed on using anti-His immunoblot. Band of interest was observed in both cell lysate and prepared microsomes fraction. The expression was verified against cell lysate and microsomes of control (FIG. 6).

Figure 7:
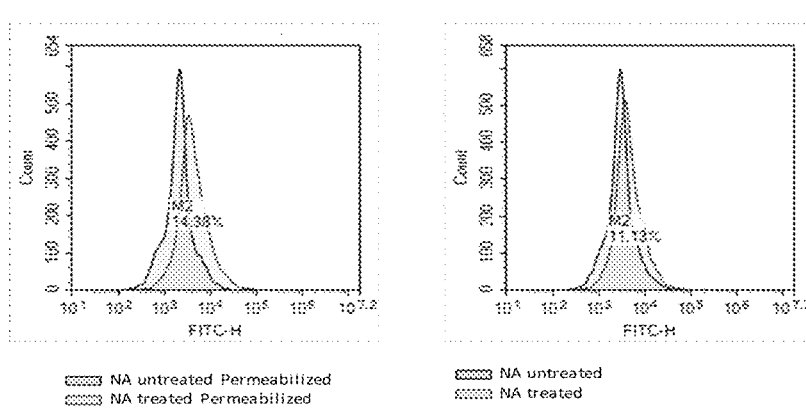
FIG. 7 shows the flow cytometry result of Neuraminidase.

Further the plasma membrane localization of protein was confirmed using Flow cytometry studies (FIG. 7).

Example 1.3: Plasma Membrane Localization of Expressed NA Analysis Using Flow Cytometry Studies Sample Preparation Yeast cells expressing plasma membrane localized NA equivalent to 1 $OD_{600\ nm}$ were taken and fixed with paraformaldehyde (4% v/v) for 15 mins of with and without Triton X100 (0.25%) for with and without permeabilization cells sample analysis. *S. cerevisiae* cells without any gene of insert were taken as control. Cells were re-suspended, washed, re-suspended and incubated in 1% BSA prepared in 1×PBS for 1 hr at 25° C.

The cells were further washed, re-suspended and incubated with 1:50 dilution of primary antibody for 1 hour at 25° C. followed by secondary antibody incubation after three washings Control cells were incubated in 1×PBS only. Centrifugation at 4000 rpm 1 min. Re-suspended the cells in secondary antibody (1:100 μl), and were incubated for 30 min at 25° C. The cells were washed with of 1×PBS by centrifugation at 4000 rpm for 1.5 minutes at 4° C. Cells were re-suspended in 2% FBS in 1×PBS and readings were taken in FACS Instruments ACEA Novo Cyte Flow Cytometer (Model: 3005). 6×His tag specific antibody was used as primary antibody and anti-mouse Alexa flour 488 labelled secondary antibody was used for the study.

Results

The Flow cytometry data showed the shift in NA expression cells for both permeabilized and non-permeabilized samples. The 11.13% in non-permeabilized cells showed the expression of NA at surface while in permeabilized cells expression was found to be more (14.38%). The result suggests the protein localizes to the cell surface (FIG. 7).

Example 1.4: Animal Studies

Analysis of immunogenic response in mice against recombinant Neuraminidase (human) expressed using *S. cerevisiae* platform.

The NA protein was enriched, as microsomes and injected in mice intramuscularly for studying the immunogenic response. For immunization, BALB/c mice were injected intramuscularly (i.m) with NA microsomal formulations in a dose volume of (50 µl having 100 µg of NA microsomes) on day 0, 14 and 28. Mice were bled retro-orbitally/tail vein after administration of Anesthesia. Total IgG, and IgM response were measured using ELISA with pre-immune, 21- and 35-day sera.

Following are the host details for checking immune response:

Test system: Mice; *Mus musculus*

Strain: Balb/c

Sex: Male

Age: 6-8 weeks

Study Design:

| | | Route of administration | Purpose | Requirement |
|---|---|---|---|---|
| | Antigen | | | |
| Immunogenic response studies | | | | |
| Balb/c | Microsomal preps | Intramuscular | Study immune response against NA | 3 mice study |

Collection of Blood Samples for Immune Assessments

In order to assess the immune response generated against the NA microsomes blood samples were collected from mice by retro-orbital bleeding after administration of anesthesia. Control serum samples were collected a day prior to the initiation of immunization. Post immunization, blood samples were collected after second immunization at 21st day and on day 35. The blood samples collected were used for serum preparation. The serum from the samples was collected and used to measure IgM and IgG response (FIG. 8 and FIG. 9) (humoral immune response).

Evaluation of the Humoral Immune Response:

The serum samples were used to measure the antibody response against the NA microsomes using ELISA. Microsomes preparations from native *S. cerevisiae* strain were used as control. ELISA plates were coated with either microsomal preparation overnight at 4° C. The plates were blocked with 1% BSA. Subsequently the serum samples were diluted appropriately and applied in duplicate and incubated at 37° C. for 1 h. The plate were subsequently washed (PBS containing 0.01% of Tween 20). Followed by secondary anti-mouse antibodies conjugated with horseradish peroxidase incubation to estimate IgG and IgM (1 h at 37° C.). The plates were developed using TMB substrate solution for color development. The reaction was stopped with 2N H2SO4, and absorbance determined at 450 nm.

Total IgG Levels at 21 and 35 Days: Sera Studies to Determine Immune Response

Figure 8:
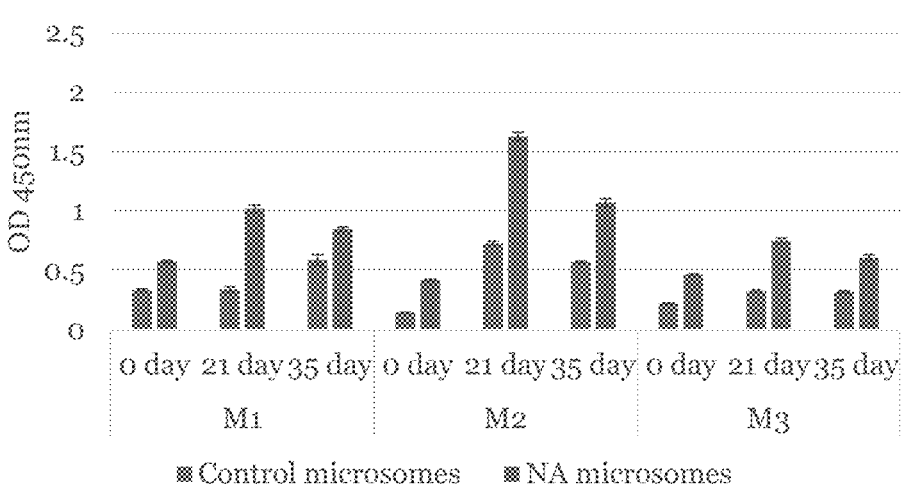
FIG. 8 shows IgM response against Neuraminidase.
Figure 9:
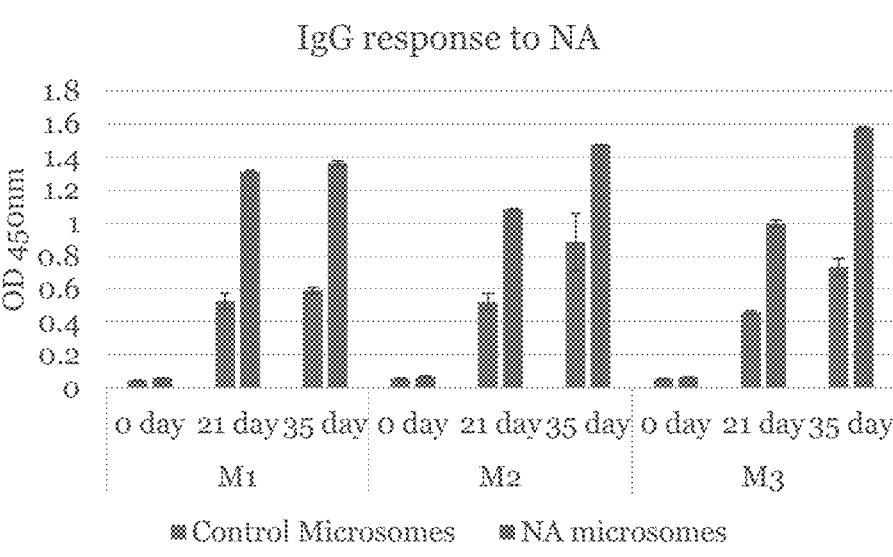
FIG. 9 shows IgG response against Neuraminidase.

To assess the immune response, NA and control microsomes were coated at a concentration of 100 ng/well for ELISA. Serum samples were diluted at 1:1000 and 1:2500 for determination of IgM and IgG response respectively (FIG. 8 and FIG. 9).

These results show that the mice injected with the NA microsomal preparations showed a specific IgM and IgG response in comparison to the control yeast cell microsomes. Thus, suggesting the NA protein in the microsomal preparations is immunogenic and elicits an immune response in mice. Thus, the NA protein from the yeast platform could be potentially used as a vaccine candidate.

Example 1.5: Culture for Microsomes Preparation

Isolated healthy patched colonies were inoculated in 100 ml of YNB Glucose—URA media as pre seed and were cultured in shaker incubator at 28° C. for 24 hr along with host strain Protease deficient strain transformed with pYRE100 as host-vector control.

Scale up culture was prepared by re inoculation in 1 litre of YNB Glucose—URA media with ~0.25 OD/ml as inoculum OD600 and were cultured in shaker incubator at 28° C. for 24 hr. The culture was harvested, and the cell pellet was induced with galactose at a final concentration of 2% in YNB—URA minimal medium. All the cultures were harvested at the 24 hr of post induction. Harvested cell pellets were used for Microsome preparation. The microsomes prepared were analyzed for expression of NA. Microsomes from the protease deficient strain were used as control.

Results depict the presence of expressed NA protein probed using anti His antibody in the Microsomes (lane 3; FIG. 6). However, no band was observed in control microsomes.

Example 1.6 Activity Assay of Neuraminidase (NA)

Microsome concentration of 5 nM, 10 nM, 25 nM and 50 nM was used for the activity assay, assuming 1% of total cell protein form the NA microsomes. 10 µl of respective concentration sample was mixed with an equal volume of assay buffer (32.5 mM 2-(N-morpholino) ethane sulfonic acid (MES), pH 6.5, containing 4 mM CaCl2). The enzymatic reaction was initiated by addition of 30 µl of 833 µM MUNANA substrate, followed by a 30 min incubation at 37° C. The reaction was terminated by the addition of 150 µl of stop solution (100 µM glycine, pH-10.7, in 25% ethanol). The amount of fluorescent product, 4-methylumbelliferone (4-MU) released was measured in a Spectra MAX Gemini EM (Molecular Devices) Fluorimeter with excitation and emission wavelengths of 355 and 460 nm respectively. Blank control reactions contained substrate alone.

All reactions were conducted in triplicate in 96-well flat-bottom opaque polystyrene plates (Corning Costar, Corning, NY, USA). A standard curve was generated by plotting relative fluorescence intensity against the amount of free 4-MU. One unit of NA was defined as one micromolar of 4-MU produced per min at 37° C. Microsome concentration was determined using Bradford's method with bovine serum albumin as standard (Bradford, 1976).

Results:

The results showed that the NA is active and saturating at the 50 nM concentration (FIG. 10). For the control, substrate without NA was used in the experiment.

Example 2: Expression of Viral Structural Capsid Protein

Example 2.1: Expression of VP7

Viral capsid protein VP7 glycoprotein a potential vaccine target was recombinantly expressed using yeast host expression platform. The gene for expression was codon biased and optimized for expression in yeast host. The protein was expressed along with a 10×His tag. The gene was cloned using conventional cloning methodologies into pYRE100 expression vector. The cloned gene was analysed through restriction digestion. The characterized construct was transformed into protease deficient *S. cerevisiae* host strain for expression studies. Expression of His tagged rVP7 was confirmed using anti-His antibody in Immunoblot analysis. The expressed platform was scaled up to 25×. Expressed protein was purified using Ni NTA chromatography and quantitated against standard.

The characterized recombinant construct was transformed in yeast host as mentioned in other examples. Few isolated healthy transformed colonies were inoculated in YNB Glucose—URA media and scaled up to culture of 475 ml was prepared and analysed for expression in 12 and 24th hr post induced (induction of late log phase; final concentration 2% galactose) time point samples. Cells were harvested and samples were prepared in 1×SDS reducing dye for expression analysis in cell pellet. The protein was characterized using anti-His antibodies immunoblot Immunoblot was developed using anti-His tag as primary antibody followed by incubation in HRP conjugated anti-mouse secondary antibody.

Results:

Band was picked at 24 h (Two clones—5 and 6) with anti-His antibody at correct size of 38 kda, Clone 6 showed a faint band at 12 hr induction sample as well, whereas no band was observed in backbone (BB) and before induction (BI) sample (FIG. 11). Using said yeast expression platform, recombinant 10×His tagged VP7 capsid protein was expressed effectually. The protein was purified using Ni NTA affinity chromatography and is described in the scale up example. Use of presently mentioned platform and similar expression and purification methodologies further showed the platform USER friendly, cost effective and timesaving approach.

Example 2.2 Scale Up of Structural Protein VP7

The protein was expressed with a 10×His tag. The negligible expression of VP7 protein was present at small scale (20 ml) (the yields were in range of 60 to 100 ng/ml). The clone was further scaled up to 25× or 500 ml scale. The expressed protein was purified using affinity chromatography, e.g., Ni NTA chromatography. Expression was analyzed on reducing SDS PAGE.

Result:

Band of interest was observed after purification. Yields were measured against BSA as standard (FIG. 12). Protein was purified with >90% purity. Obtained yield was 8 mg/L, up from 0.08 mg/ml measured basis densitometry analysis against known standard BSA.

The scalable process over a linear range of 25× volumetrically, was found to demonstrate increased yields which further describes and confirms the platform capability towards enhanced productions and suitability in producing large quantities required for various applications

Example 3: Expression of Enzyme Protein (Fatty Acid Proteins)

The enzyme gene sequence of both fatty acid desaturase and elongase was codon biased and optimized for expression in *S. cerevisiae* host. The gens were fused to 10× his tag at C terminus.

The genes were cloned using conventional cloning methodologies into proprietary expression plasmid pYRE100. The cloned genes were analysed through restriction digestion. The construct was transformed into *S. cerevisiae* host for expression studies using anti-His antibody immunoblot analysis.

Example 3.1: Process for the Expression

The characterized respective recombinant constructs were transformed using similar methodologies described for other examples. Two clones of each were expressed into proprietary protease deficient yeast expression host in rich YPD media. Expression was verified against control which was yeast transformed with episomal vector backbone.

Scale up culture of both proteins and both clones at 475 ml was produced in rich YPD media and induced using 2% galactose. 24 hrs induced cells were pelleted. The cells were resuspended in buffer and homogenized at 800 bar for 5 passes. Solution was centrifuged at 4000 rpm. The supernatant was collected without disturbing the pellet and the pellet was solubilized in same volume (as of supernatent) of urea buffer (8 M urea, 20 mM Tris, pH 8). Both proteins were expressed and are likely to be localized in ER membranes as nature. The expression was analyzed through immunoblotting analysis Immuno blot was developed using anti-His antibody as primary antibody and HRP conjugated anti-mouse secondary antibody.

Expression was observed at expected size of ~41 kda for supernatant fraction of fatty acid desaturase for one of the clones ((FIG. 13). Fatty acid elongase showed the expression in pellet at ~40 kda (expected size of 33.4 kda) for one of the clones (FIG. 14). Higher size could be due to post translational modification (glycosylation) in yeast host.

Example 3.2: Scale Up of Fatty Acid Desaturase

Further scale-up to 10× volumetric scale was performed using said platform. The scaled-up batch was set up at fermenter level with in YPD (yeast extract, peptone, and dextrose) media and induction by galactose, same as was used at 500 ml scale analysis. The process showed 10× scale up and productions of Fatty acid desaturase enzyme.

0.5 mL of pre seed culture was prepared in shaker incubator at 30° C. for 15-20 hr to a cell density ($OD_{600}$) of 3.0-4.0. The initial fermentation process was started with inoculation of media with 500 mL of seed culture. When $OD_{600}$ reached till 7-8, the temperature of the fermenter was kept at 25° C. and the culture was induced by the addition of 1 L 5×YPG (yeast extract, peptone, and galactose) solutions. DO and pH was maintained at 20% and 5.6 to 6.0.

Pellet was lysed through homogenization, solubilized and purified using Ni NTA affinity chromatography. The purified protein was characterized through SDS PAGE and anti-His tag immunoblotting (FIG. 15) Immunoblot was developed using anti-His antibody as primary antibody and HRP conjugated anti-mouse secondary antibody.

Total protein amount of 2.85 mg protein was purified from the 5 litre scale up. This clearly demonstrates scope of further yield enhancement through process development.

Example 4: Expression of Ion Channel Receptor Protein

The yeast platform herein is used to express Nav1.7 multipass transmembrane protein localized to plasma membrane, a promising drug target candidate, using protease deficient *S. cerevisiae* host strain and episomal expression vector combination.

The expressed platform was scaled up 10× times and showed consistency in yields and localization of protein. Membrane fractions were purified and analyzed as full-length protein using protein specific antibody and confocal microscopy. These purified membrane fractions have been used in literature in developing screening assays for compound screening in 96 well and 384 well formats. The scale up gives a very significant advantage of eliminating batch to batch variation in assay set up and screening data as the entire compound library or a large number of compounds can be screened using the same batch of the recombinant protein.

The principal subunit of this channel is a protein of >200 kDa, the alpha subunit. The subunit consists of four large domains of internal homology with 24 transmembrane multipass domains. The gene for expression was codon biased and optimized for expression in yeast host. The gene was cloned using conventional cloning methodologies into proprietary expression plasmid pYRE100. The cloned gene was analyzed through restriction digestion. The construct was transformed into *S. cerevisiae* protease deficient host of recombinant expression platform using anti-His antibody immunoblots analysis.

Example 4.1: Process for the Expression of Nav1.7

The characterized recombinant construct was transformed in yeast host as mentioned in example 1. Few isolated healthy transformed colonies were inoculated in 20 ml of YNB Glucose—URA media and were analyzed for expression in 24 hr post induced (Induction at late log phase A600~3.0 OD/ml; final concentration 2% galactose) time point samples using Nav1.7 protein specific antibody by Immuno-blot analysis. Selected clone was further expressed at 40 ml scale, microsomes were prepared and localization studies were done using confocal microscopy. Immunoblot was developed using Nav1.7 protein specific antibody as primary antibody followed by incubation in HRP conjugated anti-mouse secondary antibody.
Results:

Immuno Blot analysis using specific antibody showed a light band at 226 kda and higher size which could be due to glycosylation and oligomeric nature of the protein in membrane preparations (Lane 2). While minimal degradation is also seen. However, no band was observed in control (FIG. 16). It is demonstrated that complex and multipass membrane proteins which are very high impact and value drug targets can be expressed using the combination of vector and strain along with the methodologies described in this application. This allows for studying other target proteins as ion channel receptor family, GPCRs, kinases, phosphatases and so on.

Example 4.2: Confocal Microscopy Analysis for Membrane Localization of Nav1.7

Confocal microscopy confirmed the localization of Nav1.7 at the cell surface (FIG. 17). The purified protein (membranous and microsomes) could be used to screen Nav1.7 inhibitors and thus be advantageous for therapeutic purposes.

Example 5: Expression of Drug Target Molecules (GPI Anchored Protein)

The protein was expressed with a 6×His tag.

Example 5.1: Process for Expression

A single colony from the yeast selection plate was taken and put into 5 ml selection (Glucose) Media-SD with appropriate amino acids and Incubated at 30° C. with shaking for 22-24 hrs. The cultures were spun at 3500 rpm for 15 min at room temperature. The supernatant was poured off and pellets washed with sterile water. It was spun again at 3500 rpm for 15 min at 4° C. The pellet was resuspended in Yeast Peptone (Galactose) media-YPG (5 ml) for induction and incubated at 30° C. with shaking for 8 hrs. The culture was spun down at 3500 rpm for 15 min at 4° C. and pellets were lysed and analysed for protein expression. The clones were analysed using both Anti His antibody and Anti-CD 59 antibody to confirm for specific protein expression (FIG. 18). The protein was further solubilized and purified using NI-NTA column and was obtained at greater than 90% purity levels. This is an approach that has helped in establishing screening assays for compounds that bind to CD59 protein
Results:

The expression of CD-59, a glycoprotein with a GPI anchor was confirmed at small scale, 5 ml and was found to show optimum expression in 8 hr induction sample as confirmed using anti His antibody. These studies were performed at small scale and the clone was further scaled up to 200× or 1 litre scale. The expressed protein was purified using affinity chromatography, e.g. Ni NTA chromatography and was analysed on reducing SDS PAGE. Band of interest was observed after purification. Yields were measured against BSA as standard (FIG. 19).

Example 6: Scale Up Process at 500 ml Scale

Synthetic minimal media containing 2% glucose and respective selection markers were prepared in 250 mL and mixed with expression vectors pYRE100 and pYRI100 or both were incubated in shaker in case multiprotein components for expression (as per final genotype) where the parameters selected were 30±1° C., 250±10 rpm at OD600=1.5-2.0 for (16 h).

Large scale growth was performed using 2×200 mL YPD medium in 1 L shake flask at 30±1° C. and 250±10 rpm and culture was incubated to grow to OD600=4-5 (24 h) followed by induction with 2% Galactose into 2×250 mL in 1 L shake flask each 30±1° C., 250±10 rpm with OD600 for 12 h/24 hrs/36 hrs as required. The entire culture in pre weighed centrifuge bottle was centrifuged at 1000 g (3000/ 4000 rpm) for 10 minutes, 4° C. and cell pellet was weighed and stored at −80° C. till further processing to purify protein for analysis and characterization/analysis as per protein specific conditions and requirement using SDS PAGE, Immunoblot and Flow cytometry.

Table 2 below provides an overview of the scale of expression of the representative proteins through the platform of the present invention.

TABLE 2

| Sr No | Protein | Type | Scale Increase | Yield Increase |
|---|---|---|---|---|
| 1 | VP7 | Structural protein, Viral | 25x-50x | 15x-25x |
| 2 | Neuraminidase | Single pass transmembrane protein, Enzyme, Antigen Viral | 100x | 5x-10x |
| 3 | Fatty acid desaturase | Enzyme | 10x-50x | 40x-50x |
| 4 | CD59 | GPI-anchored protein | 50x-100x | 4x-10x |

Some of the important features of present expression platform are as follows:

Engineered for high expression of very low expressing proteins.

Engineered for wide applicability in proteins of different origin.

Engineered to be protease deficient.

Array of expression vectors with designed upstream regulatory sequence for enhanced expression.

Multi-engineered expression strains for varied target proteins and its intrinsic properties.

Multi protein co-expression along with codon harmonization.

Possibility of further strain optimization and engineering for increased expression of proteins.

The engineered strain can be scaled up to 500 L fermentation scale.

The present invention offers the following advantages:

Provides a versatile, robust, scalable platform for expression of conformationally active protein expression.

Can be utilized for a wide variety of proteins from different families and varied origin.

The technology can have applications in fields like vaccine development, drug discovery, metabolism, diagnostics, therapeutics and healthcare.

We claim:

1. A versatile recombinant expression platform comprising:

i. an engineered protease deficient yeast host cell with disrupted endogenous genes encoding protease PRB 1, protease PEP4 and auxotrophic markers uracil, lysine, adenine and leucine; and ii. an array of one or more episomal or integrated yeast based expression vectors operably linked with one or more promoters selected from Gal1 promoter, ADH2 promoter or Gal10 promoter, wherein the promoters can be used singly or in combination, said vector comprises a nucleic acid sequence having at least 90% sequence identity to at least one SEQ ID NO selected from: SEQ ID NOs: 7, 8, 9, 10, 11, and 12, which directs insertion of full length or truncated polynucleotide sequence into said yeast host cell for the expression of at least one target protein, and wherein said platform allows for enhanced expression of difficult to express target proteins of diverse origin and families compared to a control yeast host cell expression.

2. The recombinant expression platform as claimed in claim 1, wherein said engineered protease deficient yeast host cell with disrupted endogenous genes encoding protease PRB1, protease PEP4 and auxotrophic markers uracil, lysine, adenine and leucine is *Saccharomyces cerevisiae*.

3. The recombinant expression platform as claimed in claim 1, wherein said difficult to express proteins are from diverse origin and families selected from, but not limited to, viral, prokaryotic, eukaryotic, mammalian, human, plant, virus, algal proteins, toxins, highly hydrophobic proteins, proteins with multiple transmembrane domains, transmembrane proteins, structural proteins, non-structural proteins, drug target receptors, ion channel family, G-protein coupled receptors (GPCRs), GPI anchored proteins, enzymes, TNFR family and those localized in plasma membrane, endoplasmic reticulum, Golgi compartment and cytosol localized proteins.

4. The recombinant expression platform as claimed in claim 1, wherein said difficult to express protein is a viral protein which is a viral enzyme protein and optionally is a membrane bound Neuraminidase.

5. The recombinant expression platform as claimed in claim 1, wherein the expression of at least one target protein is selected from:

[1] a membrane bound Neuraminidase encoded by the nucleic acid sequence of SEQ ID NO: 1,

[2] a viral structural capsid protein VP7 encoded by the nucleic acid sequence of SEQ ID NO: 2,

[3] a sodium ion channel receptor Nav1.7 encoded by the nucleic acid sequence of SEQ ID NO: 3,

[4] a fatty acid desaturase encoded by the nucleic acid sequence of SEQ ID NO: 4,

[5] a fatty acid elongase encoded by the nucleic acid sequence of SEQ ID NO: 5, and

[6] a GPI anchor protein CD59 encoded by the nucleic acid sequence of SEQ ID NO: 6, and wherein said vector is an episomal expression vector comprising Ura3 auxotrophic selection marker, CYCT1 terminator, an Ampicillin resistance marker, pUC ori along with Gal1 promoter.

6. The recombinant expression platform as claimed in claim 1, wherein said difficult to express target protein is a viral structural capsid protein VP7.

7. The recombinant expression platform as claimed in claim 1, wherein said difficult to express target protein is a sodium ion channel receptor Nav1.7.

8. The recombinant expression platform as claimed in claim 1, wherein said difficult to express target protein is a fatty acid desaturase of fungal origin.

9. The recombinant expression platform as claimed in claim 1, wherein said difficult to express target protein is a fatty acid elongase.

10. The recombinant expression platform as claimed in claim 1, wherein said difficult to express target protein is a human GPI anchor protein CD59.

11. The recombinant expression platform of claim 1, wherein said platform is scalable and capable of producing proteins from diverse origin and families at an industrial scale.

12. A kit comprising the recombinant expression platform as claimed in claim 1 comprising:

i. said array of one or more episomal or integrated yeast based expression vectors encoding for difficult to express target proteins;

ii. said engineered protease deficient yeast host cells; and iii. instruction manual for operating said kit.

13. A method of producing at least one target protein selected from: a membrane bound Neuraminidase, a viral structural capsid protein VP7, a sodium ion channel receptor Nav1.7, a fatty acid desaturase, a fatty acid elongase, and a GPI anchor protein CD59, comprising the steps of:

i. preparing said array of one or more episomal or integrated yeast based expression vectors of claim 1, wherein the expression of at least one target protein is selected from:

[1] a membrane bound Neuraminidase encoded by the nucleic acid sequence of SEQ ID NO: 1,

[2] a viral structural capsid protein VP7 encoded by the nucleic acid sequence of SEQ ID NO: 2,

[3] a sodium ion channel receptor Nav1.7 encoded by the nucleic acid sequence of SEQ ID NO: 3,

[4] a fatty acid desaturase encoded by the nucleic acid sequence of SEQ ID NO: 4,

[5] a fatty acid elongase encoded by the nucleic acid sequence of SEQ ID NO: 5, and

[6] a glycosylphosphatidylinositol-anchored (GPI anchor) protein CD59 encoded by the nucleic acid sequence of SEQ ID NO: 6;

ii. transforming the said vectors in said engineered protease deficient yeast host cell of claim 1;

iii. culturing the transformed host cell of step ii for enhanced expression of at least one target protein.

14. The method according to claim 13 further comprising assessing surface localization of expressed target protein using confocal microscopy.

* * * * *

SEQUENCE LISTING

```
Sequence total quantity: 12
SEQ ID NO: 1          moltype = DNA  length = 1350
FEATURE               Location/Qualifiers
source                1..1350
                      mol_type = other DNA
                      note = Virus
                      organism = synthetic construct
SEQUENCE: 1
atgaatccaa atcagaagat aataaccatt ggatcaatct gtatggtaac tggaatagtt  60
agcttaatgt tacaaattgg gaacatgatc tcaatatggg tcagtcattc aattcacaca  120
gggaatcaac accaagctga accaatcagc aataccaatt ttcttactga gaaagctgtg  180
gcttcagtaa aattagcggg caattcatct ctttgcccca ttaacggatg ggctgtatac  240
agtaaggaca acagtataag gatcggctcc aaggggatg tgtttgttat aagagagccg  300
ttcatctcat gctcccactt ggaatgcaga actttctttt tgactcaggg agccttgctg  360
aatgacaagc actccaatgg gactgtcaaa gacagaagcc ctcacagaac attaatgagt  420
tgtcctgtgg gtgtggctcc ctccccatat aactcaaggt ttgagtctgt tgcttggtca  480
gcaagtgctt gccatgatgg caccagttgg ttgacaactt gaatttctgg cccagacaat  540
ggggctgtgg ctgtattgaa atacaatggc ataataacag acactatcaa gagttggagg  600
aacaacatat tgagaactca agagtctgaa tgtgcatgtg taaatggctc ttgctttact  660
gtaatgactg acggaccaag taatggtcaa gcatcacata agatcttcaa aatggaaaaa  720
gggaaagtgg ttaaatcagt cgaattggat gctcctaatt atcactatga ggaatgctcc  780
tgttatcctg atgccggcga aatcacgtgt gtgtgcaggg ataattggca tggctcaaat  840
cggccatggg tatctttcaa tcaaaatttg gagtatcaaa taggatatat atgcagtgga  900
gtttcggag acaatccacg ccccaatgat ggaacaggta gttgcggtcc ggtgtcctct  960
aacggggcat atggggtaaa aggattttca tttagatacg gcaatggtgt ctggatcggg  1020
agaaccaaaa gcactaattc caggagcggc tttgaaatga tttgggatcc aaatgggtgg  1080
actgaaacgg acagtagctt ttcagtgaaa caagatatcg tagcaataac tgattggtca  1140
ggatatagcg ggagttttgt ccagcatcca gaactgacag gactagattg cataagacct  1200
tgtttctggg ttgagttgat cagagggcgg cccaaagaga gcacaatttg gactagtggg  1260
agcagcatat cttttgtgg tgtaaatagt gacactgtgg gttggtcttg gccagacggt  1320
gctgagttgc cattcaccat tgacaagtag                                   1350

SEQ ID NO: 2          moltype = DNA  length = 996
FEATURE               Location/Qualifiers
source                1..996
                      mol_type = other DNA
                      note = Virus
                      organism = synthetic construct
SEQUENCE: 2
atggtttgta caactttgta cacagtttgc gctattcttt gcatcttatt agtatataca  60
ttatttctta gaaaaatgtt ccatctatta actgatgcat tagctgtttt actaatcata  120
tctgtatgtg ctggatattc taatggtcaa ttgtttacta atgatattc gtatgccgga  180
aatattgaag gtgtgataaa tacgacaaat ccttttaatg ttgagtcatt atgtatttat  240
tttccaaacg ccgcaattgg ttcaccaggt ccaggtaagg ctgatggctt attgaatgat  300
aataattatg cacagacact ggcgacatta tttgaaacaa aaggattccc gaaaggatct  360
gtgatcttta aaacatatac aaaaacatcg gacttcataa attcagtaga gatgacttgt  420
tcatataatt agtcattat tcctgatgaa ccaaagaatt cagaagcaat tgaacaaata  480
gctgaatggg tattaaatgt ttggcaatgt gatgacatga atttggatat ttatacctat  540
gaacagataa ataagataa tctgtgggca gcatttggtg aagactgtga cgtatctgtt  600
tgtccattag atacaacaat gaatgggata ggttgttcac cagctagtac agaaacatac  660
gaagtggtgt ctaatgatac tcaattggca cttatcgacg tygttgataa cgtcaaacac  720
agaattcaaa tgaatcaatt gaagtgtaaa ttgaaaaatt gcgttaaggg cgaaccacga  780
```

```
ttgaacactg caattataag aatttccaca tcatcaagct tcgacaattc gttatcacct    840
ctaaataatg gacagacaac acgaacgttc aagattaatg caaaaaaatg gtggaagatt    900
ttttatacta tagttgatta cattaataca ttggtacaaa caatgacgcc tagacatcgg    960
gctatatatc ctgaaggttg gatgctgaga tatgcg                              996

SEQ ID NO: 3              moltype = DNA   length = 5967
FEATURE                   Location/Qualifiers
source                    1..5967
                          mol_type = other DNA
                          note = Virus
                          organism = synthetic construct
SEQUENCE: 3
atggcaatgt tgcctccccc aggacctcag agctttgtcc atttcacaaa acagtctctt    60
gccctcattg aacaacgcat tgctgaaaga aaatcaaagg aacccaaaga agaaaagaaa    120
gatgatgatg aagaagcccc aaagccaagc agtgacttgg aagctggcaa acagctgccc    180
ttcatctatg gggacattcc tcccggcatg gtgtcagagc ccctggagga cttggacccc    240
tactatgcag acaaaaagac tttcatagta ttgaacaaag ggaaaacaat cttccgtttc    300
aatgccacac ctgctttata tatgctttct cctttcagtc ctctaagaag aatatctatt    360
aagattttag tacactcctt attcagcatg ctcatcatgt gcactattct gacaaactgc    420
atatttatga ccatgaataa cccaccggac tggaccaaaa atgtcgagta cacttttact    480
ggaatatata cttttgaatc acttgtaaaa atccttgcaa gaggcttctg tgtaggagaa    540
ttcacttttc ttcgtgaccc gtggaactgg ctggattttg tcgtcattgt ttttgcgtat    600
ttaacagaat ttgtaaacct aggcaatgtt tcagctcttc gaactttcag agtattgaga    660
gctttgaaaa ctatttctgt aatcccaggc ctgaagacaa ttgtaggggc tttgatccag    720
tcagtgaaga agctttctga tgtcatgatc ctgactgtgt tctgtctgag tgtgtttgca    780
ctaattggac tacagctgtt catgggaaac ctgaagcata aatgttttcg aaattcactt    840
gaaaataatg aaacattaga aagcataatg aataccctag agagtgaaga agacttttaga    900
aaatattttt attacttgga aggatccaaa gatgctctcc tttgtggttt cagcacagat    960
tcaggtcagt gtccagaggg gtacacctgt gtgaaaattg gcagaaaccc tgattatggc    1020
tacacgagct ttgacacttt cagctgggcc ttcttagcct tgtttaggct aatgacccaa    1080
gattactggg aaaacctttta ccaacagacg ctgcgtgctg ctggcaaaac ctacatgatc    1140
ttctttgtcg tagtgatttt cctgggctcc ttttatctaa taaacttgat cctggctgtg    1200
gttgccatgg catatgaaga acagaaccag gcaaacattg aagaagctaa acagaaagaa    1260
ttagaatttc aacagatgtt agaccgtctt aaaaaagagc aagaagaagc tgaggcaatt    1320
gcagcggcag cggctgaata tacaagtatt aggagaagca gaattatggg cctctcagag    1380
agttcttctg aaacatccaa actgagctct aaaagtgcta agaaagaag aaacagaaga    1440
aagaaaaaga atcaaaagaa gctctccagt ggagaggaaa agggagatgc tgagaaattg    1500
tcgaaatcag aatcagagga cagcatcaga agaaaaagtt tccaccttgg tgtcgaaggg    1560
cataggcgag cacatgaaaa gaggttgtct acccccaatc agtcaccact cagcattcgt    1620
ggctccttgt tttctgcaag gcgaagcagc agaacaagtc tttttagttt caaaggcaga    1680
ggaagagata taggatctga gactgaattt gccgatgatg agcacagcat ttttggagac    1740
aatgagagca gaaggggctc actgtttgtg ccccacagac cccaggagcg acgcagcagt    1800
aacatcagcc aagccagtag gtccccacca atgctgccgg tgaacgggaa aatgcacagt    1860
gctgtggact gcaacggtgt ggtctccctg gttgatggac gctcagccct catgctcccc    1920
aatggacagc ttctgccaga ggtgataata gataaggcaa cttctgatga cagcggcacg    1980
accaatcaaa tacacaagaa aaggcgttgt agttcctatc tcctttcaga ggatatgctg    2040
aatgatccca acctcagaca gagagcaatg agtagacaa gcatattaac aaacactgtg    2100
gaagaacttg aagagtccag acaaaaatgt ccaccttggt ggtacagatt tgcacacaaa    2160
ttcttgatct ggaattgctc tccatattgg ataaaattca aaaagtgtat ctattttatt    2220
gtaatggatc cttttgtaga tcttgcaatt accatttgca tagtttttaaa cacattattt    2280
atggctatgg aacaccaccc aatgactgag gaattcaaaa atgtacttgc tataggaaat    2340
ttggtctttta ctggaatctt tgcagctgaa atggtattaa aactgattgc catggatcca    2400
tatgagtatt tccaagtagg ctggaatatt tttgacagcc ttattgtgac tttaagttta    2460
gtggagctct ttctagcaga tgtggaagga ttgtcagttc tgcgatcatt cagactgctc    2520
cgagtcttca gttggccaaa atcctggcca acattgaaca tgctgattaa gatcattggt    2580
aactcagtag gggctctagg taacctcacc ttagtgttgg ccatcatcgt cttcattttt    2640
gctgtggtcg gcatgcagct cttttggtaag agctacaaag aatgtgtctg caagatcaat    2700
gatgactgta cgctcccacg gtggcacatg aacgacttct tccactcctt cctgattgtg    2760
ttccgcgtgc tgtgtggaga gtggatagag accatgtggg actgtatgga ggtcgctggt    2820
caagctatgt gccttattgt ttacatgatg gtcatggtca ttggaaacct ggtggtccta    2880
aacctatttc tggccttatt attgagctca tttagttcag acaatcttac agcaattgaa    2940
gaagaccctg atgcaaacaa cctccagatt gcagtgacta gaattaaaaa gggaataaat    3000
tatgtgaaac aaaccttacg tgaatttatt ctaaaagcat tttccaaaaa gccaaagatt    3060
tccagggaga taagacaagc agaagatctg aatactaaga aggaaaacta tatttctaac    3120
catacacttg ctgaaatgag caaaggtcac aatttcctca aggaaaaaga taaaatcagt    3180
ggttttggaa gcagcgtgga caaacacttg atggaagaca gtgatggtca atcatttatt    3240
cacaatccca gcctcacagt gacagtgcca attgcacctg gggaatccga tttggaaaat    3300
atgaatgctg aggaacttag cagtgattcg gatagtgaat acagcaagt gagattaaac    3360
cggtcaagct cctcagagtg cagcacagtt gataacccct tgcctggaga aggagaagaa    3420
gcagaggctg aacctatgaa ttccgatgag ccagaggcct gtttcacaga tggttgtgta    3480
tggaggttct catgctgcca agttaacata gagtcaggga aaggaaaat ctggtggaac    3540
atcaggaaaa cctgctacaa gattgttgaa cacagttggt ttgaaagctt cattgtcctc    3600
atgatcctgc tcagcagtgg tgccctggct tttgaagata tttatattga aaggaaaaag    3660
accattaaga ttatcctgga gtatgcagac aagatcttca cttacatctt cattctggaa    3720
atgcttctaa aatgggatagc atatggttat aaaacatatt tcaccaatgc ctggtgttgg    3780
ctggatttcc taattgttga tgtttctttg gttactttag tggcaaacac tcttggctac    3840
tcagatcttg gccccattaa atcccttcgg acactgagag ctttaagacc tctaagagcc    3900
ttatctgat ttgaaggaat gagggtcgtt gtgaatgcac tcataggagc aattcctct    3960
atcatgaatg tgctacttgt gtgtcttata ttctggctga tattcagcat catgggagta    4020
```

```
aatttgtttg ctggcaagtt ctatgagtgt attaacacca cagatgggtc acggtttcct   4080
gcaagtcaag ttccaaatcg ttccgaatgt tttgccctta tgaatgttag tcaaaatgtg   4140
cgatggaaaa acctgaaagt gaactttgat aatgtcggac ttggttacct atctctgctt   4200
caagttgcaa cttttaaggg atggacgatt attatgtatg cagcagtgga ttctgttaat   4260
gtagacaagc agcccaaata tgaatatagc ctctacatgt atatttattt tgtcgtcttt   4320
atcatctttg ggtcattctt cactttgaac ttgttcattg gtgtcatcat agataatttc   4380
aaccaacaga aaaagaagct tggaggtcaa gacatcttta tgacagaaga acagaagaaa   4440
tactataatg caatgaaaaa gctggggtcc aagaagccac aaaagccaat tcctcgacca   4500
gggaacaaaa tccaaggatg tatatttgac ctagtgacaa atcaagcctt tgatattagt   4560
atcatggttc ttatctgtct caacatggta accatgatgg tagaaaagga gggtcaaagt   4620
caacatatga ctgaagtttt atattggata aatgtggttt ttataatcct tttcactgga   4680
gaatgtgtgc taaaactgat ctccctcaga cactactact tcactgtagg atggaatatt   4740
tttgattttg tggttgtgat tatctccatt gtaggtatgt ttctagctga tttgattgaa   4800
acgtattttg tgtcccctac cctgttccga gtgatccgtc ttgccaggat tggccgaatc   4860
ctacgtctag tcaaaggagc aaaggggatc cgcacgctgc tctttgcttt gatgatgtcc   4920
cttcctgcgt tgtttaacat cggcctcctg ctcttcctgg tcatgttcat ctacgccatc   4980
tttggaatgt ccaactttgc ctatgttaaa aaggaagatg gaattaatga catgttcaat   5040
tttgagacct ttggcaacag tatgatttgc ctgttccaaa ttacaacctc tgctggctgg   5100
gatggattgc tagcacctat tcttaacagt aagccacccg actgtgaccc aaaaaaagtt   5160
catcctggaa gttcagttga aggagactgt ggtaacccat ctgttggaat attctacttt   5220
gttagttata tcatcatatc cttcctggtt gtggtgaaca tgtacattgc agtcatactg   5280
gagaatttta gtgttgccac tgaagaaagt actgaacctc tgagtgagga tgactttgag   5340
atgttctatg aggtttggga gaagtttgat cccgatgcga cccagtttat agagttctct   5400
aaaactctctg attttgcagc tgccctggat cctcctcttc tcatagcaaa acccaacaaa   5460
gtccagctca ttgccatgga tctgcccatg gttagtggtg accggatcca ttgtcttgac   5520
atcttatttg cttttacaaa gcgtgttttg ggtgagagtg gggagatgga ttctcttcgt   5580
tcacagatgg aagaaaggtt catgtctgca aatccttcca aagtgtccta tgaacccatc   5640
acaaccacac taaaacggaa acaagaggat gtgtctgcta ctgtcattca gcgtgcttat   5700
agacgttacc gcttaaggca aaatgtcaaa aatatatcaa gtatatacat aaaagatgga   5760
gacagagatg atgatttact caataaaaaa gatatggctt ttgataatgt taatgagaac   5820
tcaagtccag aaaaaacaga tgccacttca tccaccacct ctccaccttc atatgatagt   5880
gtaacaaagc cagacaaaga gaaatatgaa caagacagaa cagaaaagga agacaaaggg   5940
aaagacagca aggaaagcaa aaaatag                                       5967
```

```
SEQ ID NO: 4            moltype = DNA   length = 1086
FEATURE                 Location/Qualifiers
source                  1..1086
                        mol_type = other DNA
                        note = Fungi
                        organism = synthetic construct
SEQUENCE: 4
atggctacaa aggaggctta cgtttttccca actctcaccg agatcaagag atctctccca   60
aaggattgct tcgaggcttc tgtgcctttg tctctctact acactgtgag atgcttggtt   120
attgctgtgg ctttgacctt cggattgaac tacgctagag ctttgccaga ggttgagtct   180
ttctgggctt tggatgctgc tttgtgcact ggatatatcc tcctccaggg aattgtgttc   240
tggggattct tcactgttgg acacgatgct ggacacggag ctttctctag ataccacctc   300
ttgaacttcg ttgtgggaac cttcatgcac tctctcatct tgacccccatt cgagtcttgg   360
aagttgaccc acagacacca ccacaagaac accggaaaca tcgatagaga tgaggtgttc   420
tacccacaga gaaaggctga tgatcaccca ttgtccagga acttgatctt ggctttggga   480
gctgcttggc ttgcttattt ggtggaggga ttcccaccaa gaaaggtgaa ccacttcaac   540
ccattcgagc cacttttttgt gagacaagtg tccgctgtgg ttatctcttt gctcgctcac   600
ttcttcgttg ctggactctc tatctacttg tctctccagt tgggacttaa gaccatggct   660
atctactact acgaccagt tttcgtgttc ggatctatgt tggtgattac caccttcttg   720
caccacaacg atgaggagac tccatggtat gctgattctg agtggactta cgtgaaggga   780
aacttgtcct ctgtggatag atcttacggt gctctcataa ataacctctc ccacaacatc   840
ggaactcacc agatccacca cctcttccca attatcccac actacaagct caagaaggct   900
actgctgctt ccaccaaagc tttcccccag cttgtgagaa agtccgatga gccaatcatc   960
aaggctttct tcagagtggg aaggttgtat gctaactacg gagtggttga tcaagaggct   1020
aagctcttca ctttgaagga ggctaaggct gctactgaag ctgctgctaa gaccaagtct   1080
acctga                                                              1086
```

```
SEQ ID NO: 5            moltype = DNA   length = 873
FEATURE                 Location/Qualifiers
source                  1..873
                        mol_type = other DNA
                        note = Plant
                        organism = synthetic construct
SEQUENCE: 5
atggaagttg ttgagaggtt ctacggagag ttggatggaa aggtttccca aggagtgaac   60
gctttgttgg gatctttcgg agttgagttg actgataccc caactactaa gggattgcca   120
ctcgttgatt ctccaactcc aattgtgttg ggagtgtctg tttacttgac catcgtgatc   180
ggaggattgc tttggatcaa ggctagagat ctcaagccaa gagcttctga gccattcttg   240
ttgcaagctt tggtgttggt gcacaacttg ttctgcttcg ctttgtctct ttacatgtgc   300
gtgggtatcg cttaccaagc tatcacctcg agatattcct tgtggggaaa cgcttataac   360
ccaaagcaca aggagatggc tatcctcgtt tacctcttct acatgtccaa gtacgtggag   420
ttcatggata ccgtgatcat gatcctcaag agatccacca gacagatttc tttcctccac   480
gtgtaccacc actcttctat ctcccttatc tggtgggcta ttgctcacca cgctccagga   540
ggagaggctt attggagtgc tgctctcaac tctgagtgc acgtgttgat gtacgcttac   600
tacttcttgg ctgcttgctt gagatcttcc ccaaagctca agaacaagta cctcttctgg   660
```

```
ggaagatacc tcacccaatt ccagatgttc cagttcatgc tcaacttggt gcaagcttac   720
tacgatatga aaaccaacgc tccatatcca caatggctca tcaagatcct cttctactac   780
atgatctccc tcttgttcct cttcggaaac ttctacgtgc aaaagtacat caagccatcc   840
gatggaaagc aaaagggagc taagaccgag tga                                873

SEQ ID NO: 6              moltype = DNA   length = 405
FEATURE                  Location/Qualifiers
source                   1..405
                         mol_type = other DNA
                         note = Human
                         organism = synthetic construct
SEQUENCE: 6
atgggaatcc aaggagggtc tgtcctgttc gggctgctgc tcgtcctggc tgtcttctgc    60
cattcaggtc atagccatca ccatcaccat cacctgcagt gctacaactg tcctaaccca   120
actgctgact gcaaaacagc cgtcaattgt tcatctgatt ttgatgcgtg tctcattacc   180
aaagctgggt tacaagtgta taacaagtgt tggaagtttg agcattgcaa tttcaacgac   240
gtcacaaccc gcttgaggga aaatgagcta acgtactact gctgcaagaa ggacctgtgt   300
aactttaacg aacagcttga aaatggtggg acatccttat cagagaaaac agttcttctg   360
ctggtgactc catttctggc agcagcctgg agccttcatc cctaa                   405

SEQ ID NO: 7              moltype = DNA   length = 6657
FEATURE                  Location/Qualifiers
source                   1..6657
                         mol_type = other DNA
                         note = Virus
                         organism = synthetic construct
SEQUENCE: 7
cgcgtgtacg catgtaacat tatactgaaa accttgcttg agaaggtttt gggacgctcg    60
aaggctttaa tttgcaagct gcggccctgc attaatgaat cggccaacgc gcggggagag   120
gcggtttgcg tattgggcgc tcttccgctt cctcgctcac tgactcgctg cgctcggtcg   180
ttcggctgcg gcgagcggta tcagctcact caaaggcggt aatacggtta tccacagaat   240
cagggggataa cgcaggaaag aacatgtgag caaaaggcca gcaaaagccc aggaaccgta   300
aaaaggccgc gttgctggcg tttttccata ggctccgccc ccctgacgag catcacaaaa   360
atcgacgctc aagtcagagg tggcgaaacc cgacaggact ataaagatac caggcgtttc   420
cccctggaag ctccctcgtg cgctctcctg ttccgaccct gccgcttacc ggatacctgt   480
ccgcctttct cccttcggga agcgtggcgc tttctcatag ctcacgctgt aggtatctca   540
gttcggtgta ggtcgttcgc tccaagctgg gctgtgtgca cgaaccccc gttcagcccg    600
accgctgcgc cttatccggt aactatcgtc ttgagtccaa cccggtaaga cacgacttat   660
cgccactggc agcagccact ggtaacagga ttagcagagc gaggtatgta ggcggtgcta   720
cagagttctt gaagtggtgg cctaactacg gctacactag aaggacagta tttggtatct   780
gcgctctgct gaagccagtt accttcggaa aaagagttgg tagctcttga tccggcaaac   840
aaaccaccgc tggtagcggt ggtttttttg tttgcaagca gcagattacg cgcagaaaaa   900
aaggatctca agaagatcct ttgatctttt ctacggggtc tgacgctcag tggaacgaaa   960
actcacgtta agggattttg gtcatgagat tatcaaaaag gatcttcacc tagatccttt  1020
taaattaaaa atgaagtttt aaatcaatct aaagtatata tgagtaaact tggtctgaca  1080
gttaccaatg cttaatcagt gaggcaccta tctcagcgat ctgtctattt cgttcatcca  1140
tagttgcctg actccccgtc gtgtagataa ctacgatacg ggagggctta ccatctggcc  1200
ccagtgctgc aatgataccg cgagacccac gctcaccggc tccagattta tcagcaataa  1260
accagccagc cggaagggcc gagcgcagaa gtggtcctgc aactttatcc gcctccatcc  1320
agtctattaa ttgttgccgg gaagctagag taagtagttc gccagttaat agtttgcgca  1380
acgttgttgg cattgctaca ggcatcgtgg tgtcactctc gtcgtttggt atggcttcat  1440
tcagctccgg ttcccaacga tcaaggcgag ttacatgatc ccccatgttg tgcaaaaaag  1500
cggttagctc cttcggtcct ccgatcgttg tcagaagtaa gttggccgca gtgttatcac  1560
tcatggttat ggcagcactg cataattctc ttactgtcat gccatccgta agatgctttt  1620
ctgtgactgg tgagtactca accaagtcat tctgagaata gtgtatgcgg cgaccgagtt  1680
gctcttgccc ggcgtcaata cgggataata gtgtatcaca tagcagaact ttaaaagtgc  1740
tcatcattgg aaaacgttct cggggcgaa aactctcaag gatcttaccg ctgttgagat   1800
ccagttcgat gtaacccact cgtgcaccca actgatcttc agcatctttt actttcacca  1860
gcgtttctgg gtgagcaaaa acaggaaggc aaaatgccgc aaaaaaggga ataagggcga  1920
cacggaaatg ttgaatactc atactcttcc ttttttcaatg ggtaataact gatataatta  1980
aattgaagct ctaatttgtg agtttagtat acatgcattt acttataata cagttttttta  2040
gttttgctgg ccgcatcttc tcaaatatgc ttcccagcct gcttttctgt aacgttcacc  2100
ctctacctta gcatcccttc cctttgcaaa tagtcctctt ccaacaataa taatgtcaga  2160
tcctgtagag accacatcat ccacggttct atactgttga gtccaatgct ctcccttgtc  2220
atctaaaccc acaccgggtg tcataatcaa ccaatcgtaa ccttcatctc ttccacccat  2280
gtctctttga gcaataaagc cgataacaaa atctttgtcg ctcttcgcaa tgtcaacagt  2340
acccttagta tattctccag tagataggga gcccttgcat gacaattctg ctaacatcaa  2400
aaggcctcta ggttcctttg ttacttcttc tgccgcctgc ttcaaaccgc taacaatacc  2460
tgggcccacc acaccgtgtg cattcgtaat gtctgcccat tctgctattc tgtatacacc  2520
cgcagagtac tgcaatttga ctgtattacc aatgtcagca aattttctgt cttcgaagag  2580
taaaaaattg tacttggcgg ataatgcctt tagcggctta actgtgccct ccatggaaaa  2640
atcagtcaag atatccacat gtgttttag taaacaaatt ttgggaccta atgcttcaac   2700
taactccagt aattccttgg tggtacgaac atccaatgaa gcacacaagt ttgtttgctt  2760
ttcgtgcatg atattaaata gcttggcagc aacaggacta ggatgagtag cagcacgttc  2820
cttatatgta gctttcgaca tgatttatct tcgtttcctg caggtttttg ttctgtgcag  2880
ttgggttaag aatactgggc aatttcatgt ttcttcaaca ctacatatgc gtatatatac  2940
caatctaagt ctgtgctcct tccttcgttc ttccttctgt tcggagatta ccgaatcaaa  3000
aaaatttcaa agaaaccgaa atcaaaaaaa agaataaaaa aaaatgatg aattgaattg   3060
aaaagctagc ttatcgatga taagctgtca aagatgagaa ttaattccac ggactataga  3120
```

-continued

```
ctatactaga tactccgtct actgtacgat acacttccgc tcaggtcctt gtcctttaac    3180
gaggccttac cactctttg ttactctatt gatccagctc agcaaaggca gtgtgatcta    3240
agattctatc ttcgcgatgt agtaaaacta gctagaccga gaaagagact agaaatgcaa    3300
aaggcacttc tacaatggct gccatcatta ttatccgatg tgacgctgca gcttctcaat    3360
gatattcgaa tacgctttga ggagatacag cctaatatcc gacaaactgt tttacagatt    3420
tacgatcgta cttgttaccc atcattgaat tttgaacatc cgaacctggg agttttccct    3480
gaaacagata gtatatttga acctgtataa taatatatag tctagcgctt tacggaagac    3540
aatgtatgta tttcggttcc tggagaaact attgcatcta ttgcataggt aatcttgcac    3600
gtcgcatccc cggttcattt tctgcgtttc catcttgcac ttcaatagca tatctttgtt    3660
aacgaagcat ctgtgcttca ttttgtagaa caaaaatgca acgcgagagc gctaattttt    3720
caaacaaaga atctgagctg cattttaca gaacagaaat gcaacgcgaa agcgctattt    3780
taccaacgaa gaatctgtgc ttcattttgt aaaacaaaa atgcaacgcg acgagagcgc    3840
taatttttca aacaaagaat ctgagctgca ttttttacaga acagaaatgc aacgcgagag    3900
cgctattta ccaacaaaga atctatactt cttttttgtt ctacaaaat gcatcccgag    3960
agcgctattt ttctaacaaa gcatcttaga ttactttttt tctcctttgt gcgctctata    4020
atgcagtctc ttgataactt tttgcactgt aggtccgtta aggttagaag aaggctactt    4080
tggtgtctat tttctcttcc ataaaaaaag cctgactcca cttcccgcgt ttactgatta    4140
ctagcgaagc tgcgggtgca ttttttcaag ataaaggcat ccccgattat attctatacc    4200
gatgtggatt gcgcatactt tgtgaacaga aagtgatagc gttgatgatt cttcattggt    4260
cagaaaatta tgaacggttt cttctatttt gtctctatat actacgtata ggaaatgttt    4320
acattttcgt attgttttcg attcactcta tgaatagttc ttactacaat tttttttgtct    4380
aaagagtaat actagagata aacataaaaa atgtagaggt cgagtttaga tgcaagttca    4440
aggagcgaaa ggtggatggg taggttatat agggatatag cacagagata tatagcaaag    4500
agatacttt gagcaatgtt tgtggaagcg gtattcgcaa tgggaagctc caccccggtt    4560
gataatcaga aaagccccaa aaacaggaag attgtataag caaatattta aattccggaa    4620
cggcgcgcac ggattagaag ccgccgagcg ggtgacagcc ctccgaagga agactctcct    4680
ccgtgcgtcc tcgtcttcac cggtcgcgtt cctgaaacgc agatgtgcct cgcgccgcac    4740
tgctccgaac aataaagatt ctacaatact agcttttatg gttatgaaga ggaaaaattg    4800
gcagtaacct ggccccacaa accttcaaat gaacgaatca aattaacaac cataggatga    4860
taatgcgatt agttttttag ccttatttct ggggtaatta atcagcgaag cgatgatttt    4920
tgatctatta acagatatat aaatgcaaaa actgcataac cactttaact aatactttca    4980
acattttcgg tttgtattac ttcttattca aatgtaataa aagtatcaac aaaaaattgt    5040
taatatacct ctatacttta acgtcaagga gaaaaaaccg atatcgaatt catgaatcca    5100
aatcagaaga taataaccat tggatcaatc tgtatggtaa ctggaatagt tagcttaatg    5160
ttacaaattg ggaacatgat ctcaatatgg gtcagtcatt caattccac agggaatcaa    5220
caccaagctg aaccaatcag caataccaat tttcttactg agaaagctgt ggcttcagta    5280
aaattagcgg gcaattcatc tctttgcccc attaacggat gggctgtata cagtaaggac    5340
aacagtataa ggatcggctc caaggggat gtgtttgtta aagagagcc gttcatctca    5400
tgctcccact tggaatgcag aactttcttt ttgactcagg gagccttgct gaatgacaag    5460
cactccaatg ggactgtcaa agacagaagc cctcacagaa cattaatgag ttgtcctgtg    5520
ggtgtggctc cctccccata taactcaagg tttgagtctg ttgcttggtc agcaagtgct    5580
tgccatgatg gcaccagttg gttgacaatt ggaatttctg gcccagacaa tgggctgtg    5640
gctgtattga aatacaatgg cataataaca gacactatca agagtttggag gaacaacata    5700
ttgagaactc aagagtctga atgtgcatgt gtaaatggct cttgctttac tgtaatgact    5760
gacgggaccaa gtaatggtca agcatcacat aagatcttca aaatggaaaa agggaaagtg    5820
gttaaatcag tcgaattgga tgctcctaat tatcactatg aggaatgctc ctgttatcct    5880
gatgccggcg aaatcacgtg tgtgtgcagg gataattggc atggctcaaa tcggccatgg    5940
gtatctttca atcaaaattt ggagtatcaa ataggatata tatgcagtgg agttttcgga    6000
gacaatccac gccccaatga tggaacaggt agttgcggtc cggtgtcctc taacgggggca    6060
tatgggtaa aaggattttc atttagatac ggcaatggtg tctggatcgg agaaccaaa    6120
agcactaatt ccaggagcgg ctttgaaatg atttgggatc caaatgggtg gactgaaacg    6180
gacagtagct tttcagtgaa acaagatatc gtagcaataa ctgattggtc aggatatagc    6240
gggagttttg tccagcatcc agaactgaca ggactagatt gcataagacc ttgtttctgg    6300
gttgagttga tcagagggcg gcccaaagag agcacaattt ggactagtgg gagcagcata    6360
tcttttgtg gtgtaaatag tgacactgtg ggttggtctt ggccagacgg tgctgagttg    6420
ccattcacca ttgacaagct cgagcatcat caccatcacc attaaagatc tctgcaggat    6480
atcatcatgt aattagttat gtcacgctta cattcacgcc ctcccccac atccgctcta    6540
accgaaaagg aaggagttag acaacctgaa gtctaggtcc ctatttattt ttttatagtt    6600
atgttagtat taagaacgtt atttatattt caaatttttc ttttttttct gtacaga    6657
```

```
SEQ ID NO: 8          moltype = DNA   length = 6444
FEATURE               Location/Qualifiers
source                1..6444
                      mol_type = other DNA
                      note = Virus
                      organism = synthetic construct
SEQUENCE: 8
cgcgtgtacg catgtaacat tatactgaaa accttgcttg agaaggtttt gggacgctcg    60
aaggctttaa tttgcaagct gcggccctgc attaatgaat cggccaacgc gcggggagag    120
gcggtttgcg tattgggcgc tcttccgctt cctcgctcac tgactcgctg cgctcggtcg    180
ttcggctgcg gcgagcggta tcagctcact caaaggcggt aatacggtta tccacagaat    240
caggggataa cgcaggaaag aacatgtgag caaaaggcca gcaaaagccc aggaaccgta    300
aaaaggccgc gttgctggcg tttttccata ggctccgccc cctgacgag catcacaaaa    360
atcgacgctc aagtcagagg tggcgaaacc cgacaggact ataaagatac caggcgttc    420
cccctggaag ctccctcgtg cgctctcctg ttccgaccct gccgcttacc ggatacctgt    480
ccgcctttct cccttcggga agcgtggcgc tttctcatag ctcacgctgt aggtatctca    540
gttcggtgta ggtcgttcgc tccaagctgg gctgtgtgca cgaaccccc gttcagcccg    600
accgctgcgc cttatccggt aactatcgtc ttgagtccaa cccggtaaga cacgacttat    660
cgccactggc agcagccact ggtaacagga ttagcagagc gaggtatgta ggcggtgcta    720
```

-continued

```
cagagttctt gaagtggtgg cctaactacg gctacactag aaggacagta tttggtatct    780
gcgctctgct gaagccagtt accttcggaa aaagagttgg tagctcttga tccggcaaac    840
aaaccaccgc tggtagcggt ggttttttg tttgcaagca gcagattacg cgcagaaaaa    900
aaggatctca agaagatcct ttgatctttt ctacgggggtc tgacgctcag tggaacgaaa    960
actcacgtta agggattttg gtcatgagat tatcaaaaag gatcttcacc tagatccttt   1020
taaattaaaa atgaagtttt aaatcaatct aaagtatata tgagtaaact tggtctgaca   1080
gttaccaatg cttaatcagt gaggcaccta tctcagcgat ctgtctattt cgttcatcca   1140
tagttgcctg actcccgtc gtgtagataa ctacgtacg ggagcgctta ccatctggcc   1200
ccagtgctgc aatgataccg cgagacccac gctcaccggc tccagattta tcagcaataa   1260
accagccagc cggaagggcc gagcgcagaa gtggtcctgc aactttatcc gcctccatcc   1320
agtctattaa ttgttgccgg gaagctagag taagtagttc gccagttaat agtttgcgca   1380
acgttgttgg cattgctaca ggcatcgtgg tgtcactctc gtcgtttggt atggcttcat   1440
tcagctccgg ttcccaacga tcaaggcgag ttacatgatc ccccatgttg tgcaaaaaag   1500
cggttagctc cttcggtcct ccgatcgttg tcagaagtaa gttggccgca gtgttatcac   1560
tcatggttat ggcagcactg cataattctc ttactgtcat gccatccgta agatgctttt   1620
ctgtgactgg tgagtactca accaagtcat tctgagaata gtgtatgcgg cgaccgagtt   1680
gctcttgccc ggcgtcaata cgggataata gtgtatcaca tagcagaact ttaaaagtgc   1740
tcatcattgg aaaacgttct cggggggcgaa aactctcaag atcttaccg ctgttgagat   1800
ccagttcgat gtaacccact cgtgcaccca actgatcttc agcatctttt actttcacca   1860
gcgtttctgg gtgagcaaaa acaggaaggc aaaatgccgc aaaaaaggga ataagggcga   1920
cacggaaatg ttgaatactc atactcttcc tttttcaatg ggtaataact gatataatta   1980
aattgaagct ctaatttgtg agtttagtat acatgcattt acttataata cagttttta   2040
gttttgctgg ccgcatcttc tcaaatatgc ttcccagcct gcttttctgt aacgttcacc   2100
ctctacctta gcatcccttc cctttgcaaa tagtcctctt ccaacaataa taatgtcaga   2160
tcctgtagag accacatcat ccacggttct atactgttga cccaatgcgt ctcccttgtc   2220
atctaaaccc acaccgggtg tcataatcaa ccaatcgtaa ccttcatctc ttccacccat   2280
gtctctttga gcaataaagc cgataacaaa atctttgtcg ctcttcgcaa tgtcaacagt   2340
acccttagta tattctccag tagataggga gcccttgcat gacaattctg ctaacatcaa   2400
aaggcctcta ggttcctttg ttacttcttc tgccgcctgc ttcaaaccgc taacaatacc   2460
tgggcccacc acaccgtgtg cattcgtaat gtctgcccat tctgctattc tgtatacacc   2520
cgcagagtac tgcaatttga ctgtattacc aatgtcagca aattttctgt cttcgaagag   2580
taaaaaattg tacttggcgg ataatgcctt tagcggctta actgtgccct ccatggaaaa   2640
atcagtcaag atatccacat gtgttttag taaacaaatt ttgggaccta atgcttcaac   2700
taactccagt aattccttgg tggtacgaac atccaatgaa gcacacaagt ttgtttgctt   2760
ttcgtgcatg atattaaata gcttggcagc aacaggacta ggatgagtag cagcacgttc   2820
cttatatgta gctttcgaca tgatttatct tcgtttcctg caggttttg ttctgtgcag   2880
ttgggttaag aatactgggc aatttcatgt ttcttcaaca ctacatatgc gtatatatac   2940
caatctaagt ctgtgctcct tccttcgttc ttccttctgt tcggagatta ccgaatcaaa   3000
aaaatttcaa agaaaccgaa atcaaaaaaa agaataaaaa aaaaatgatg aattgaattg   3060
aaaagctagc ttatcgatga taagctgtca aagatgagaa ttaattccac ggactataga   3120
ctatactaga tactccgtct actgtacgat acacttccgc tcaggtcctt gtcctttaac   3180
gaggccttac cactcttttg ttactctatt gatccagctc agcaaaggca gtgtgatcta   3240
agattctatc ttcgcgatgt agtaaaacta gctagaccga gaaagagact agaaatgcaa   3300
aaggcacttc tacaatggct gccatcatta ttatccgatg tgacgctgca gcttctcaat   3360
gatattcgaa tacgctttga ggagatacag cctaatatcc gacaaactgt tttacagatt   3420
tacgatcgta cttgttaccc atcattgaat tttgaacatc cgaacctggg agtttttccct   3480
gaaacagata gtatatttga acctgtataa taatatatag tctagcgctt tacggaagac   3540
aatgtatgta tttcggttcc tggagaaact attgcatcta ttgcataggt aatcttgcac   3600
gtcgcatccc cggttcattt tctgcgtttc catcttgcac ttcaatagca tatctttgtt   3660
aacgaagcat ctgtgcttca ttttgtagaa caaaaatgca acgcgagagc gctaatttttt   3720
caaacaaaga atctgagctg catttttaca gaacagaaat gcaacgcgaa gcgctatttt   3780
taccaacgaa gaatctgtgc ttcattttttg taaaacaaaa atgcaacgcg acgagagcgc   3840
taattttttca aacaaagaat ctgagctgca ttttttacaga acagaaatgc aacgcgagag   3900
cgctattttta ccaacaaaga atctatactt cttttttgtt ctacaaaaat gcatcccgag   3960
agcgctattt ttctaacaaa gcatcttaga ttacttttttt tctcctttgt gcgctctata   4020
atgcagtctc ttgataactt tttgcactgt aggtccgtta aggttagaag aaggctactt   4080
tggtgtctat tttctcttcc ataaaaaaag cctgactcca cttcccgcgt ttactgatta   4140
ctagcgaagc tgcgggtgca tttttttcaag ataaaggcat ccccgattat attctatacc   4200
gatgtggatt gcgcatactt tgtgaacaga aagtgatagc gttgatgatt cttcattggt   4260
cagaaaatta tgaacggttt cttctatttt gtctctatat actacgtata ggaaatgttt   4320
acattttcgt attgttttcg attcactcta tgaatagttc ttactacaat ttttttgtct   4380
aaagagtaat actagagata aacataaaaa atgtagaggt cgagtttaga tgcaagttca   4440
aggagcgaaa ggtggatggg taggttatat agggatatag cacagagata tatagcaaag   4500
agatactttt gagcaatgtt tgtggaagcg gtattcgcaa ggggagagtc caccccggaa   4560
gataatcaga aaagccccaa aaacaggaag attgtataag caaatattta aattccggaa   4620
cggcgcgcac ggattagaag ccgccgagcg ggtgacagcc ctccgaagga gactctcct   4680
ccgtgcgtcc tcgtcttcac cggtcgcgtt cctgaaacgc agatgtgcct cgcgccgcac   4740
tgctccgaac aataaagatt ctacaatact agcttttatg gttatgaaga ggaaaaattg   4800
gcagtaacct ggccccacaa accttcaaat gaacgaatca aattaacaac cataggatga   4860
taatgcgatt agtttttttag ccttatttct ggggtaatta atcagcgaag cgatgatttt   4920
tgatctatta acagatatat aaatgcaaaa actgcataac cactttaact aatactttca   4980
acattttcgg tttgtattac ttcttattca aatgtaataa aagtatcaac aaaaaattgt   5040
taatatacct ctatacttta acgtcaagga gaaaaaaccg atatcgaatt cggatccaag   5100
cttacataca aaatgtttg tacaactttg tacacagtt tgcatttt ttgcatctca   5160
ttagtatata cattatttct tagaaaaatg ttccatctat taactgatgc attagctgtt   5220
ttactaatca tatctgtatg tgctggatat tctaatggtc aattgtttac taatgatatt   5280
tcgtatgccg gaaatattga aggtgtgata aatacgacaa atcctttaa tgttgagtca   5340
ttatgtattt attttccaaa cgccgcaatt ggttcaccag gtccaggtaa ggctgatggc   5400
ttattgaatg ataataatta tgcacagaca ctggcgacat tatttgaaac aaaaggattc   5460
```

```
ccgaaaggat ctgtgatctt taaaacatat acaaaaacat cggacttcat aaattcagta  5520
gagatgactt gttcatataa tttagtcatt attcctgatg aaccaaagaa ttcagaagca  5580
attgaacaaa tagctgaatg ggtattaaat gtttggcaat gtgatgacat gaatttggat  5640
atttatacct atgaacagat aaataaagat aatctgtggg cagcatttgg tgaagactgt  5700
gacgtatctg tttgtccatt agatacaaca atgaatggga taggttgttc accagctagt  5760
acagaaacat acgaagtggt gtctaatgat actcaattgg cacttatcga cgtygttgat  5820
aacgtcaaac acagaattca aatgaatcaa ttgaagtgta aattgaaaaa ttgcgttaag  5880
ggcgaaccac gattgaacac tgcaattata agaatttcca catcatcaag cttcgacaat  5940
tcgttatcac ctctaaataa tggacagaca acacgaacgt tcaagattaa tgcaaaaaaa  6000
tggtggaaga ttttttatac tatagttgat tacattaata cattggtaca aacaatgacg  6060
cctagacatc gggctatata tcctgaaggt tggatgctga gatatgcggg tggtggtggt  6120
tctcatcatc accaccacca tcatcaccat cattaataag gtaccccaca attgtggggc  6180
ccgggcgcta gctgtacacc acaattgtgg tctagagcta agcagctcga gcatcatcac  6240
catcaccatt aaagatctct gcaggatatc atcatgtaat tagttatgtc acgcttacat  6300
tcacgccctc cccccacatc cgctctaacc gaaaaggaag gagttagaca acctgaagtc  6360
taggtcccta tttatttttt tatagttatg ttagtattaa gaacgttatt tatatttcaa  6420
atttttcttt ttttctgta caga                                          6444
```

```
SEQ ID NO: 9               moltype = DNA  length = 11310
FEATURE                    Location/Qualifiers
source                     1..11310
                           mol_type = other DNA
                           note = Virus
                           organism = synthetic construct
SEQUENCE: 9
cgcgtgtacg catgtaacat tatactgaaa accttgcttg agaaggtttt gggacgctcg  60
aaggctttaa tttgcaagct gcggccctgc attaatgaat cggccaacgc gcggggagag  120
gcggtttgcg tattgggcgc tcttccgctt cctcgctcac tgactcgctg cgctcggtcg  180
ttcggctgcg gcgagcggta tcagctcact caaaggcggt aatacggtta ccacagaat  240
caggggataa cgcaggaaag aacatgtgag caaaaggcca gcaaaagccc aggaaccgta  300
aaaaggccgc gttgctggcg tttttccata ggctccgccc ccctgacgag catcacaaaa  360
atcgacgctc aagtcagagg tggcgaaacc cgacaggact ataaagatac caggcgtttc  420
cccctggaag ctccctcgtg cgctctcctg ttccgaccct gccgcttacc ggatacctgt  480
ccgcctttct cccttcggga agcgtggcgc tttctcatag ctcacgctgt aggtatctca  540
gttcggtgta ggtcgttcgc tccaagctgg gctgtgtgca cgaaccccc gttcagcccg  600
accgctcgc cttatccggt aactatcgtc ttgagtccaa cccggtaaga cacgacttat  660
cgccactggc agcagccact ggtaacagga ttagcagagc gaggtatgta ggcggtgcta  720
cagagttctt gaagtggtgg cctaactacg gctacactag aaggacagta tttggtatct  780
gcgctctgct gaagccagtt accttcggaa aaagagttgg tagctcttga tccggcaaac  840
aaaccaccgc tggtagcggt ggtttttttg tttgcaagca gcagattacg cgcagaaaaa  900
aaggatctca agaagatcct ttgatctttt ctacggggtc tgacgctcag tggaacgaaa  960
actcacgtta agggattttg gtcatgagat tatcaaaaag gatcttcacc tagatccttt  1020
taaattaaaa atgaagtttt aaatcaatct aaagtatata tgagtaaact tggtctgaca  1080
gttaccaatg cttaatcagt gaggcaccta tctcagcgat ctgtctattt cgttcatcca  1140
tagttgcctg actccccgtc gtgtagataa ctacgatacg ggagcgctta ccatctggcc  1200
ccagtgctgc aatgataccg cgagacccac gctcaccggc tccagattta tcagcaataa  1260
accagccagc cggaagggcc gagcgcagaa gtggtcctgc aactttatcc gcctccatcc  1320
agtctattaa ttgttgccgg gaagctagag taagtagttc gccagttaat agtttgcgca  1380
acgttgttgg cattgctaca ggcatcgtgg tgtcactctc gtcgtttggt atggcttcat  1440
tcagctccgg ttcccaacga tcaaggcgag ttacatgatc ccccatgttg tgcaaaaaag  1500
cggttagctc cttcggtcct ccgatcgttg tcagaagtaa gttggccgca gtgttatcac  1560
tcatggttat ggcagcactg cataattctc ttactgtcat gccatccgta agatgctttt  1620
ctgtgactgg tgagtactca accaagtcat tctgagaata gtgtatgcgg cgaccgagtt  1680
gctcttgccc ggcgtcaata cgggataata gtgtatcaca tagcagaact ttaaaagtgc  1740
tcatcattgg aaaacgttct cggggcgaa aactctcaag gatcttaccg ctgttgagat  1800
ccagttcgat gtaacccact cgtgcaccca actgatcttc agcatctttt actttcacca  1860
gcgtttctgg gtgagcaaaa acaggaaggc aaaatgccgc aaaaaaggga ataagggcga  1920
cacgaaatg ttgaatactc atactcttcc tttttcaatg ggtaataact gatataatta  1980
aattgaagct ctaatttgtg agtttagtat acatgcattt acttataata cagtttttta  2040
gtttttgctgg ccgcatcttc tcaaatatgc ttcccagcct gcttttctgt aacgttcacc  2100
ctctacctta gcatcccttc cctttgcaaa tagtcctctt ccaacaataa taatgtcaga  2160
tcctgtagag accacatcat ccacggttct atactgttga cccaatgcgt ctcccttgtc  2220
atctaaaccc acaccgggtg tcataatcaa ccaatcgtaa ccttcatctc ttccacccat  2280
gtctctttga gcaataaagc cgataacaaa atctttgtcg ccttctcgca tgtcaacagt  2340
acccttagta tattccag tagatagga gcccttgcat gacaattctg ctaacatcaa  2400
aaggcctcta ggttcctttg ttacttcttc tgccgcctgc ttcaaaccgc taacaatacc  2460
tgggcccacc acaccgtgtg cattcgtaat gtctgcccat tctgctattc tgtatacacc  2520
cgcagagtac tgcaatttga ctgtattacc aatgtcagca aattttctgt cttcgaagag  2580
taaaaaattg tacttggcgg ataatgcctt tagcggctta actgtgccct ccatggaaaa  2640
atcagtcaag atatccacat gtgttttag taaacaaatt ttgggaccta atgcttcaac  2700
taactccagt aattccttgg tggtacgaac atccaatgaa gcacacaagt ttgtttgctt  2760
ttcgtgcatt atattaaata gcttggcagc aacaggacta ggatgagtag cagcacgttc  2820
cttatatgta gctttcgaca tgatttatct tcgtttcctg caggttttg ttctgtgcag  2880
ttgggttaag aatactgggc aatttcatgt ttcttcaaca ctacatatgc gtatatatac  2940
caatctaagt ctgtgctcct tccttcgttc ttccttctgt tcggagatta ccgaatcaaa  3000
aaaatttcaa agaaccgaa atcaaaaaaa agaataaaaa aaaatgatg aattgaattg  3060
aaaagctagc ttatcgatga taagctgtca aagatgagaa ttaattccac ggactataga  3120
ctatactaga tactccgtct actgtacgat acacttccgc tcaggtcctt gtcctttaac  3180
gaggccttac cactctttg ttactctatt gatccagctc agcaaaggca gtgtgatcta  3240
```

-continued

```
agattctatc ttcgcgatgt agtaaaacta gctagaccga gaaagagact agaaatgcaa    3300
aaggcacttc tacaatggct gccatcatta ttatccgatg tgacgctgca gcttctcaat    3360
gatattcgaa tacgctttga ggagatacag cctaatatcc gacaaactgt tttacagatt    3420
tacgatcgta cttgttaccc atcattgaat tttgaacatc cgaacctggg agttttccct    3480
gaaacagata gtatatttga acctgtataa taatatatag tctagcgctt tacggaagac    3540
aatgtatgta tttcggttcc tggagaaact attgcatcta ttgcataggt aatcttcgac    3600
gtcgcatccc cggttcattt tctgcgtttc catcttgcac ttcaatagca tatctttgtt    3660
aacgaagcat ctgtgcttca ttttgtagaa caaaaatgca acgcgagagc gctaattttt    3720
caaacaaaga atctgagctg cattttaca gaacagaat gcaacgcgaa agcgctattt    3780
taccaacgaa gaatctgtgc ttcattttg taaaacaaaa atgcaacgcg acgagagcgc    3840
taatttttca aacaaagaat ctgagctgca tttttacaga acagaaatgc aacgcgagag    3900
cgctatttta ccaacaaaga atctatactt ctttttttgtt ctacaaaat gcatcccgag    3960
agcgctattt ttctaacaaa gcatcttaga ttactttttt tctccttttgt gcgctctata    4020
atgcagtctc ttgataactt tttgcactgt aggtccgtta aggttagaag aaggctactt    4080
tggtgtctat tttctcttcc ataaaaaaag cctgactcca cttcccgcgt ttactgatta    4140
ctagcgaagc tgcgggtgca ttttttcaag ataaaggcat ccccgattat attctatacc    4200
gatgtggatt gcgcatactt tgtgaacaga aagtgatagc gttgatgatt cttcattggt    4260
cagaaaatta tgaacggttt cttctatttt gtctctatat actacgtata ggaaatgttt    4320
acattttcgt attgttttcg attcactcta tgaatagttc ttactacaat tttttttgtct    4380
aaaagagtaat actagagata aacataaaaa atgtagaggt cgagtttaga tgcaagttca    4440
aggagcgaaa ggtggatggg taggttatat agggatatag cacagagata tatagcaaag    4500
agatactttt gagcaatgtt tgtggaagcg gtattcgcaa ggaagctc caccccggtt    4560
gataatcaga aaagccccaa aaacaggaag attgtataag caaatattta aattccggaa    4620
cggcgcgcac ggattagaag ccgccgagcg ggtgacagcc ctccgaagga agactctcct    4680
ccgtgcgtcc tcgtcttcac cggtcgcgtt cctgaaacgc agatgtgcct cgcgccgcac    4740
tgctccgaac aataaagatt ctacaatact agcttttatg gttatgaaga ggaaaaattg    4800
gcagtaacct ggccccacaa accttcaaat gaacgaatca aattaacaac cataggatga    4860
taatgcgatt agttttttag ccttatttct ggggtaatta atcagcgaag cgatgatttt    4920
tgatctatta acagatatat aaatgcaaaa actgcataac cactttaact aatactttca    4980
acattttcgg tttgtattac ttcttattca aatgtaataa aagtatcaac aaaaaattgt    5040
taatatacct ctatacttta acgtcaagga gaaaaaaccg atatcgaatt cggatccaca    5100
tacaaaatgg caatgttgcc tcccccagga cctcagagct ttgtccattt cacaaaacag    5160
tctcttgccc tcattgaaca acgcattgct gaaagaaat caaaggaacc caagaagaa    5220
aagaaaatg atgatgaaga agccccaaag ccaagcagtg acttggaagc tggcaaacag    5280
ctgcccttca tctatgggga cattcctccc ggcatggtgt cagagcccct ggaggacttg    5340
gaccccctact atgcagacaa aaagactttc atagtattga acaaagggaa aacaatcttc    5400
cgtttcaatg ccacacctgc tttatatatg cttttctcctt tcagtcctct aagaagaata    5460
tctattaaga tttttagtaca ctccttattc agcatgctca tcatgtgcac tattctgaca    5520
aactgcatat ttatgaccat gaataaccca ccggactgga ccaaaaatgt cgagtacact    5580
tttactggaa tatatacttt tgaatcactt gtaaaaatcc ttgcaagagg cttctgtgta    5640
ggagaattca ctttttcttcg tgacccgtgg aactggctgg attttgtcgt cattgttttt    5700
gcgtatttaa cagaatttgt aaacctaggc aatgtttcag ctcttcgaac tttcagagta    5760
ttgagagctt tgaaaactat ttctgtaatc ccaggcctga agacaattgt aggggctttg    5820
atccagtcag tgaagaagct ttctgatgtc atgatcctga ctgtgttctg tctgagtgtg    5880
tttgcactaa ttggactaca gctgttcatg ggaaacctga agcataaatg ttttcgaaat    5940
tcacttgaaa ataatgaaac attagaaagc ataatgaata ccctagagag tgaagaagac    6000
tttagaaaat atttttatta cttggaagga tccaaagatg ctctccttttg tggtttcagc    6060
acagattcag gtcagtgtcc agaggggtac acctgtgtga aaattggcag aaacctgat    6120
tatggctaca cgagctttga cactttcagc tgggcttct tagccttgtt taggctaatg    6180
acccaagatt actgggaaaa cctttaccaa cagacgctgc gtgctgctgg caaaacctac    6240
atgatcttct ttgtcgtagt gatttttcctg ggctcctttt atctaataaa cttgatcctg    6300
gctgtggttg ccatggcata tgaagaacag aaccaggcaa acattgaaga agctaaacag    6360
aaagaattag aatttcaaca gatgttagac cgtcttaaaa aagagcaaga agaagctgag    6420
gcaattgcag cggcagcggc tgaatataca agtattagga gaagcagaat tatgggcctc    6480
tcagagagtt cttctgaaac atccaaactg agctctaaaa gtgctaaaga aagaagaaac    6540
agaagaaaga aaaagaatca aaagaagctc tccagtggag aggaaaaggg agatgctgag    6600
aaattgtcga aatcagaatc agaggacagc atcagaagaa aaagtttcca ccttggtgtc    6660
gaagggcata ggcgagcaca tgaaaagagg ttgtctaccc ccaatcagtc accactcagc    6720
attcgtggct ccttgtttttc tgcaaggcga agcagcagaa caagtctttt tagtttcaaa    6780
ggcagaggaa gagatatagg atctgagact gaatttgccg atgatgagca cagcattttt    6840
ggagacaatg agagcagaag gggctcactg tttgtgcccc acagacccca ggagcgacgc    6900
agcagtaaca tcagccaagc cagtaggtcc ccaccaatgc tgccggtgaa cgggaaaatg    6960
cacagtgctg tggactgcaa cggtgtggtc tccctggttg atggacgctc agccctcatg    7020
ctccccaatg gacagcttct gccagaggtc ataatgagata aggcaacttc tgatgacgac    7080
ggcacgacca atcaaataca caagaaaagg cgttgtagtt cctatctcct ttcagaggat    7140
atgctgaatg atcccaacct cagacagaga gcaatgagta gagcaagcat attaacaaac    7200
actgtggaag aacttgaaga gtccagacaa aaatgtccac cttggtggta cagatttgca    7260
cacaaattct tgatctggaa ttgctctcca tattggataa aattcaaaaa gtgtatctat    7320
tttattgtaa tggatccttt tgtagatctt gcaattacca tttgcatagt tttaaacaca    7380
ttatttatgg ctatgaacaa ccacccaatg actgaggaat tcaaaaatgt acttgctata    7440
ggaaatttgg tctttactgg aatcttttgca gctgaaatgg tattaaaact gattgccatg    7500
gatccatatg agtatttcca gtaggctgg aatatttttg acagccttat tgtgacttta    7560
agtttagtgg agctctttct agcagatgtg gaaggattgc agttctgcg atcattcaga    7620
ctgctccgag tcttcaagtt ggcaaaatcc tggccaacat tggccatgct gattaagatc    7680
attggtaact cagtagggggc tctaggtaac ctcaccttag tgttggccat catcgtcttc    7740
attttttgctg tggtcggcat gcagctcttt ggtaagagct acaaagaatg tgtctgcaag    7800
atcaatgatg actgtacgct cccacggtgg cacatgaacg acttcttcca ctcctttcctg    7860
attgtgttcc gcgtgctgtg tggagagtgg atagagacca tgtgggactg tatggaggtc    7920
gctggtcaag ctatgtgcct tattgtttac atgatggtca tggtcattgg aaacctggtg    7980
```

-continued

```
gtcctaaacc tatttctggc cttattattg agctcattta gttcagacaa tcttacagca   8040
attgaagaag accctgatgc aaacaacctc cagattgcag tgactagaat taaaaaggga   8100
ataaattatg tgaaacaaac cttacgtgaa tttattctaa aagcattttc caaaaagcca   8160
aagatttcca gggagataag acaagcagaa gatctgaata ctaagaagga aaactatatt   8220
tctaaccata cacttgctga aatgaacaaa ggtcacaatt tcctcaagga aaaagataaa   8280
atcagtggtt ttggaagcag cgtggacaaa cacttgatgg aagacagtga tggtcaatca   8340
tttattcaca atcccagcct cacagtgaca gtgccaattg cacctgggga atccgatttg   8400
gaaaatatga atgctgagga acttagcagt gattcggata gtgaatacag caaagtgaga   8460
ttaaaccggt caagctcctc agagtgcagc acagttgata acccttttgcc tggacaagga   8520
gaagaagcag aggctgaacc tatgaattcc gatgagccag aggcctgttt cacagatggt   8580
tgtgtatgga ggtctcatg ctgccaagtt aacatagagt cagggaaagg aaaaatctgg   8640
tggaacatca ggaaaacctg ctacaagatt gttgaacaca gttggtttga aagcttcatt   8700
gtcctcatga tcctgctcag cagtggtgcc ctggcttttg aagatattta tattgaaagg   8760
aaaaagacca ttaagattat cctggagtat gcagacaaga tcttcactta catcttcatt   8820
ctggaaatgc ttctaaaatg gatagcatat ggttataaaa catatttcac caatgcctgc   8880
tgttggctgg atttcctaat tgttgatgtt tctttggtta ctttagtggc aaacactctt   8940
ggctactcag atcttggccc cattaaatcc cttcggacac tgagagcttt aagacctcta   9000
agagccttat ctagatttga aggaatgagg gtcgttgtga atgcactcat aggagcaatt   9060
ccttccatca tgaatgtgct acttgtgtgt cttatattct ggctgatatt cagcatcatg   9120
ggagtaaatt tgtttgctgg caagttctat gagtgtatta acaccacaga tgggtcacgg   9180
tttcctgcaa gtcaagttcc aaatcgttcc gaatgttttg cccttatgaa tgttagtcaa   9240
aatgtgcgat ggaaaaacct gaaagtgaac tttgataatg tcggacttgg ttacctatct   9300
ctgcttcaag ttgcaacttt taagggatgg acgattatta tgtatgcagc agtggattcc   9360
gttaatgtag acaagcagcc caaatatgaa tatagcctct acatgtatat ttattttgtc   9420
gtctttatca tctttgggtc attcttcact ttgaacttgt tcattggtgt catcatagat   9480
aatttcaacc aacagaaaaa gaagcttgga ggtcaagaca tctttatgac agaagaacag   9540
aagaaatact ataatgcaat gaaaaagctg gggtccaaga agccacaaaa gccaattcct   9600
cgaccaggga acaaaatcca aggatgtata tttgacctag tgacaaatca agcctttgat   9660
attagtatca tggttcttat ctgtctcaac atggtaacca tgatggtaga aaaggagggt   9720
caaagtcaac atatgactga agttttatat tggataaatg tggtttttat aatcctttttc   9780
actggagaat gtgtgctaaa actgatctcc ctcagacact actacttcac tgtaggatgg   9840
aatattttttg attttgtggt tgtgattatc tccattgtag gtatgtttct agctgatttg   9900
attgaaacgt attttgtgtc ccctaccctg ttccgagtga tccgtcttgc caggattggc   9960
cgaatcctac gtctagtcaa aggagcaaag gggatccgca cgctgctctt tgctttgatg   10020
atgtcccttc ctgcgttgtt taacatcggc ctcctgctct tcctggtcat gttcatctac   10080
gccatctttg gaatgtccaa cttttgcctat gttaaaaagg aagatggaat taatgacatg   10140
ttcaattttg agacctttgg caacagtatg atttgcctgt tccaaattac aacctctgct   10200
ggctgggatg gattgctagc acctattctt aacagtaagc cacccgactg tgacccaaaa   10260
aaagttcatc ctggaagttc agttgaagga gactgtggta acccatctgt tggaatattc   10320
tactttgtta gttatatcat catatccttc ctggttgtgg tgaacatgta cattgcagtc   10380
atactggaga attttagtgt tgccactgaa gaaagtactg aacctctgag tgaggatgac   10440
tttgagatgt tctatgaggt ttgggagaag tttgatcccg atgcgaccca gtttatagag   10500
ttctctaaac tctctgattt tgcagctgcc ctggatccctc ctcttctcat agcaaaaccc   10560
aacaaagtcc agctcattgc catggatctg cccatggtta gtggtgaccg gatccattgt   10620
cttgacatct tatttgcttt tacaaagcgt gttttgggtg agagtgggga gatggaattct   10680
cttcgttcac agatggaaga aaggttcatg tctgcaaatc cttccaaagt gtcctatgaa   10740
cccatcacaa ccacactaaa acggaaacaa gaggatgtgt ctgctactgt cattcagcgt   10800
gcttatagac gttaccgctt aaggcaaaat gtcaaaaata tatcaagtat atacataaaa   10860
gatggagaca gagatgatga tttactcaat aaaaaagata tggctttttga taatgttaat   10920
gagaactcaa gtccagaaaa aacagatgcc acttcatcca ccacctctcc accttcatat   10980
gatagtgtaa caaagccaga caaagagaaa tatgaacaag acagaacaga aaaggaagac   11040
aaagggaaag acagcaagga aagcaaaaaa tagtaatcta gagctaagca gctcgagcat   11100
catcaccatc accattaaag atctctgcag gatatcatca tgtaattagt tatgtcacgc   11160
ttacattcac gccctccccc cacatccgct ctaaccgaaa aggaaggagt tagacaacct   11220
gaagtctagg tccctatttta tttttttata gttatgttag tattaagaac gttatttata   11280
tttcaaattt ttcttttttt tctgtacaga                                     11310
```

SEQ ID NO: 10          moltype = DNA   length = 6531
FEATURE                Location/Qualifiers
source                 1..6531
                       mol_type = other DNA
                       note = Fungi
                       organism = synthetic construct
SEQUENCE: 10

```
cgcgtgtacg catgtaacat tatactgaaa accttgcttg agaaggtttt gggacgctcg   60
aaggctttaa tttgcaagct gcggccctgc attaatgaat cggccaacgc gcggggagag   120
gcggtttgcg tattgggcgc tcttccgctt cctcgctcac tgactcgctg cgctcggtcg   180
ttcggctgcg gcgagcggta tcagctcact caaaggcggt aatacggtta tccacagaat   240
cagggggataa cgcaggaaag aacatgtgag caaaaggcca gcaaaaggcc aggaaccgta   300
aaaaggccgc gttgctggcg ttttttccata ggctccgccc ccctgacgag catcacaaaa   360
atcgacgctc aagtcagagg tggcgaaacc cgacaggact ataaagatac caggcgtttc   420
cccctggaag ctccctcgtg cgctctcctg ttccgaccct gccgcttacc ggatacctgt   480
ccgcctttct cccttcggga agcgtggcgc tttctcatag ctcacgctgt aggtatctca   540
gttcggtgta ggtcgttcgc tccaagctgg gctgtgtgca cgaaccccc gttcagcccg   600
accgctgcgc cttatccggt aactatcgtc ttgagtccaa cccggtaaga cacgacttat   660
cgccactggc agcagccact ggtaacagga ttagcagagc gaggtatgta ggcggtgcta   720
cagagttctt gaagtggtgg cctaactacg gctacactag aaggacagta tttggtatct   780
gcgctctgct gaagccagtt accttcggaa aaagagttgg tagctcttga tccggcaaac   840
aaaccaccgc tggtagcggt ggtttttttg tttgcaagca gcagattacg cgcagaaaaa   900
```

-continued

```
aaggatctca agaagatcct ttgatctttt ctacggggtc tgacgctcag tggaacgaaa    960
actcacgtta agggattttg gtcatgagat tatcaaaaag gatcttcacc tagatccttt   1020
taaattaaaa atgaagtttt aaatcaatct aaagtatata tgagtaaact tggtctgaca   1080
gttaccaatg cttaatcagt gaggcaccta tctcagcgat ctgtctattt cgttcatcca   1140
tagttgcctg actccccgtc gtgtagataa ctacgatacg ggagcgctta ccatctggcc   1200
ccagtgctgc aatgataccg cgagaccac gctcaccggc tccagattta tcagcaataa   1260
accagccagc cggaagggcc gagcgcagaa gtggtcctgc aactttatcc gcctccatcc   1320
agtctattaa ttgttgccgg gaagctagag taagtagttc gccagttaat agtttgcgca   1380
acgttgttgg cattgctaca ggcatcgtgg tgtcactctc gtcgtttggt atggcttcat   1440
tcagctccgg ttcccaacga tcaaggcgag ttacatgatc ccccatgttg tgcaaaaaag   1500
cggttagctc cttcggtcct ccgatcgttg tcagaagtaa gttggccgca gtgttatcac   1560
tcatggttat ggcagcactg cataattctc ttactgtcat gccatccgta agatgctttt   1620
ctgtgactgg tgagtactca accaagtcat tctgagaata gtgtatgcgg cgaccgagtt   1680
gctcttgccc ggcgtcaata cgggataata gtgtatcaca tagcagaact ttaaaagtgc   1740
tcatcattgg aaaacgttct cggggccgaa aactctcaag gatcttaccg ctgttgagat   1800
ccagttcgat gtaacccact cgtgcaccca actgatcttc agcatctttt actttcacca   1860
gcgtttctgg gtgagcaaaa acaggaaggc aaaatgccgc aaaaaaggga ataagggcga   1920
cacggaaatg ttgaatactc atactcttcc tttttcaatg ggtaataact gatataatta   1980
aattgaagct ctaatttgtg agtttagtat acatgcattt acttataata cagttttta    2040
gttttgctgg ccgcatcttc tcaaatatgc ttcccagcct gcttttctgt aacgttcacc   2100
ctctacctta gcatcccttc cctttgcaaa tagtcctctt ccaacaataa taatgtcaga   2160
tcctgtagag accacatcat ccacggttct atactgttga ccaatgcgt ctcccttgtc    2220
atctaaaccc acaccgggtg tcataatcaa ccaatcgtaa ccttcatctc ttccacccat   2280
gtctctttga gcaataaagc cgataacaaa atctttgtcg ctcttcgcaa tgtcaacagt   2340
accttagta tattctccag tagatagga gcccttgcat gacaattctg ctaacatcaa    2400
aaggcctcta ggttcctttg ttacttcttc tgccgcctgc ttcaaaccgc taacaatacc   2460
tgggcccacc acaccgtgtg cattcgtaat gtctgcccat tctgctattc tgtatacacc   2520
cgcagagtac tgcaatttga ctgtattacc aatgtcagca aattttctgt cttcgaagag   2580
taaaaaattg tacttggcgg ataatgcctt tagcggctta actgtgccct ccatggaaaa   2640
atcagtcaag atatccacat gtgtttttag taaacaaatt ttgggaccta atgcttcaac   2700
taactccagt aattccttgg tggtacgaac atccaatgaa gcacacaagt ttgtttgctt   2760
ttcgtgcatg atattaaata gcttggcagc aacaggacta ggatgagtag cagcacgttc   2820
cttatatgta gctttcgaca tgatttatct tcgtttcctg caggtttttg ttctgtgcag   2880
ttgggttaag aatactgggc aatttcatgt ttcttcaaca ctacatatgc gtatatatac   2940
caatctaagt ctgtgctcct tccttcgttc ttccttctgt tcggagatta ccgaatcaaa   3000
aaaatttcaa agaaaccgaa atcaaaaaaa agaataaaaa aaaaatgatg aattgaattg   3060
aaaagctagc ttatcgatga taagctgtca aagatgagaa ttaattccac ggactataga   3120
ctatactaga tactccgtct actgtacgat acacttccgc tcaggtcctt gtcctttaac   3180
gaggccttac cactctttg ttactctatt gatccagctc agcaaaggca gtgtgatca    3240
agattctatc ttcgcgatgt agtaaaacta gctagaccga gaaagagact agaaatgcaa   3300
aaggcacttc tacaatggct gccatcatta ttatccgatg tgacgctgca gcttctcaat   3360
gatattcgaa tacgctttga ggagatacag cctaatatcc gacaaactgt tttacagatt   3420
tacgatcgta cttgttaccc atcattgaat tttgaacatc cgaacctgga agttttccct   3480
gaaacagata gtatatttga acctgtataa taatatatag tctagcgctt tacggaagac   3540
aatgtatgta tttcggttcc tggagaaact attgcatcta ttgcataggt aatcttgcac   3600
gtcgcatccc cggttcattt tctgcgtttc catcttcac ttcaatagca tatctttgtt    3660
aacgaagcat ctgtgcttca ttttgtagaa caaaaatgca acgcgagagc gctaattttt   3720
caaacaaaga atctgagctg catttttaca gaacagaaat gcaacgcgaa agcgctattt   3780
taccaacgaa gaatctgtgc ttcatttttg taaaacaaaa atgcaacgcg acgagagcgc   3840
taatttttca aacaaagaat ctgagctgca ttttttacaga acagaaatgc aacgcgagag   3900
cgctatttta ccaacaaaga atctatactt cttttttgtt ctacaaaaat gcatcccgag   3960
agcgctattt ttctaacaaa gcatcttaga ttactttttt tctccttgt gcgctctata    4020
atgcagtctc ttgataactt tttgcactgt aggtccgtta aggttagaag aaggctactt   4080
tggtgtctat tttctcttcc ataaaaaaag cctgactcca cttcccgcgt ttactgatta   4140
ctagcgaagc tgcgggtgca ttttttcaag ataaaggcat ccccgattat attctatacc   4200
gatgtggatt gcgcatactt tgtgaacaga aagtgatagc gttgatgatt cttcattggt   4260
cagaaaatta tgaacggttt cttctatttt gtctctatat actacgtata ggaaatgttt   4320
acattttcgt attgttttcg attcactcta tgaatagttc ttactacaat tttttgtct    4380
aaagagtaat actagagata aacataaaaa atgtagaggt cgagtttaga tgcaagttca   4440
aggagcgaaa ggtggatggg taggttatat agggatatag cacagagata tataggcaaag   4500
agatactttt gagcaatgtt tgtggaagcg gtattcgcaa tgggaagctc cacccccggtt   4560
gataatcaga aaagccccaa aaacaggaag attgtataag caaatattta aattccggaa   4620
cggcgcgcac ggattagaag ccgccgagcg ggtgacagcc ctccgaagga agactctcct   4680
ccgtgcgtcc tcgtcttcac cggtcgcgtt cctgaaacgc agatgtgcct cgcgccgcac   4740
tgctccgaac aataaagatt ctacaatact agctttttatg gttatgaaga ggaaaaattg   4800
gcagtaacct ggccccacaa accttcaaat gaacgaatca aattaacaac cataggatga   4860
taatgcgatt agtttttttag ccttatttct ggggtaatta atcagcgaag cgatgatttt   4920
tgatctatta acagatatat aaatgcaaaa actgcataac cactttaact aatactttca   4980
acattttcgg tttgtattac ttcttattca aatgtaataa agtatcaac aaaaaaattgt    5040
taatataacct ctatacttta acgtcaagga gaaaaaaccg atatcgaatt cggatccaag   5100
cttacataca aaatggctac aaaggaggct tacgttttcc caactctcac cgagatcaag   5160
agatctctcc caaaggattg cttcgaggct tctgtgcctt tgtctctcta ctacactgtg   5220
agatgcttgg ttattgctgt ggctttgacc ttcggattga actacgctag agctttgcca   5280
gaggttgaat ctttctgggc tttggatatt ctggtatat cctcctccag                5340
ggaattgtgt tctgggggatt cttcactgtt ggacacgatg ctggacacgg agctttctct   5400
agataccacc tcttgaactt cgttgtggga accttcatgc actctctcat cttgacccca    5460
ttcgagtctt ggaagttgac ccacagacac caccacaaga acaccggaaa catcgataga   5520
gatgaggtgt tctacccaca gagaaaggct gatgatcacc cattgtccag gaacttgatc   5580
ttggctttgg gagctgcttg gcttgcttat ttggtggagg gattcccacc aagaaaggtg   5640
```

```
aaccacttca acccattcga gccactttttt gtgagacaag tgtccgctgt ggttatctct    5700
ttgctcgctc acttcttcgt tgctggactc tctatctact tgtctctcca gttgggactt    5760
aagaccatgg ctatctacta ctacggacca gttttcgtgt tcggatctat gttggtgatt    5820
accaccttct tgcaccacaa cgatgaggag actccatggt atgctgattc tgagtggact    5880
tacgtgaagg gaaacttgtc ctctgtggat agatcttacg gtgctctcat cgataacctc    5940
tcccacaaca tcggaactca ccagatccac cacctcttcc caattatccc acactacaag    6000
ctcaagaagg ctactgctgc tttccaccaa gctttcccag agcttgtgag aaagtccgat    6060
gagccaatca tcaaggcttt cttcagagtg ggaaggttgt atgctaacta cggagtggtt    6120
gatcaagagg ctaagctctt cactttgaag gaggctaagg ctgctactga agctgctgct    6180
aagaccaagt ctaccggtgg tggtggttct catcatcacc accaccatca tcaccatcat    6240
taataaggta ccccacaatt gtggggcccg ggcgctagct gtacaccaca attgtggtct    6300
agagctaagc agctcgagca tcatcaccat caccattaaa gatctctgca ggatatcatc    6360
atgtaattag ttatgtcacg cttacattca cgccctcccc ccacatccgc tctaaccgaa    6420
aaggaaggag ttagacaacc tgaagtctag gtccctattt attttttttat agttatgtta    6480
gtattaagaa cgttatttat atttcaaatt tttctttttt ttctgtacag a             6531
```

SEQ ID NO: 11                 moltype = DNA  length = 6318
FEATURE                       Location/Qualifiers
source                        1..6318
                              mol_type = other DNA
                              note = Plant
                              organism = synthetic construct
SEQUENCE: 11

```
cgcgtgtacg catgtaacat tatactgaaa accttgcttg agaaggtttt gggacgctcg     60
aaggctttaa tttgcaagct gcggccctgc attaatgaat cggccaacgc gcggggagag    120
gcggtttgcg tattgggcgc tcttccgctt cctcgctcac tgactcgctg cgctcggtcg    180
ttcggctgcg gcgagcggta tcagctcact caaaggcggt aatacggtta cccacagaat    240
cagggggataa cgcaggaaag aacatgtgag caaaaggcca gcaaaagccc aggaaccgta    300
aaaaggccgc gttgctggcg ttttttccata ggctccgccc ccctgacgag catcacaaaa    360
atcgacgctc aagtcagagg tggcgaaacc cgacaggact ataaagatac caggcgtttc    420
ccccctggaag ctccctcgtg cgctctcctg ttccgaccct gccgcttacc ggatacctgt    480
ccgcctttct cccttcggga agcgtggcgc tttctcatag ctcacgctgt aggtatctca    540
gttcggtgta ggtcgttcgc tccaagctgg gctgtgtgca cgaaccccccc gttcagcccg    600
accgctggcg ccttatccggt aactatcgtc ttgagtccaa cccggtaaga cacgacttat    660
cgccactggc agcagccact ggtaacagga ttagcagagc gaggtatgta ggcggtgcta    720
cagagttctt gaagtggtgg cctaactacg gctacactag aaggacagta tttggtatct    780
gcgctctgct gaagccagtt accttcggaa aaagagttgg tagctcttga tccggcaaac    840
aaaccaccgc tggtagcggt ggttttttttg tttgcaagca gcagattacg cgcagaaaaa    900
aaggatctca agaagatcct ttgatctttt ctacggggtc tgacgctcag tggaacgaaa    960
actcacgtta agggattttg gtcatgagat tatcaaaaag gatcttcacc tagatccttt    1020
taaattaaaa atgaagtttt aaatcaatct aaagtatata tgagtaaact tggtctgaca    1080
gttaccaatg cttaatcagt gaggcaccta tctcagcgat ctgtctattt cgttcatcca    1140
tagttgcctg actccccgtc gtgtagataa ctacgatacg ggagggctta ccatctggcc    1200
ccagtgctgc aatgataccg cgagacccac gctcaccggc tccagattta tcagcaataa    1260
accagccagc cggaagggcc gagcgcagaa gtggtcctgc aactttatcc gcctccatcc    1320
agtctattaa ttgttgccgg gaagctagag taagtagttc gccagttaat agtttgcgca    1380
acgttgttgg cattgctaca ggcatcgtgg tgtcactcgt gtcgtttggt atggcttcat    1440
tcagctccgg ttcccaacga tcaaggcgag ttacatgatc ccccatgttg tgcaaaaaag    1500
cggttagctc cttcggtcct ccgatcgttg tcagaagtaa gttggccgca gtgttatcac    1560
tcatggttat ggcagcactg cataattctc ttactgtcat gccatccgta agatgctttt    1620
ctgtgactgg tgagtactca accaagtcat tctgagaata gtgtatgcgg cgaccgagtt    1680
gctcttgccc ggcgtcaata cgggataata ccgcgccaca tagcagaact ttaaaagtgc    1740
tcatcattgg aaaacgttct cggggcgaaa actctcaag gatcttaccg ctgttgagat    1800
ccagttcgat gtaacccact cgtgcaccca actgatcttc agcatctttt actttcacca    1860
gcgtttctgg gtgagcaaaa acaggaaggc aaaatgccgc aaaaaaggga ataagggcga    1920
cacggaaatg ttgaatactc atactcttcc ttttttcaatg ggtaataact gatataatta    1980
aattgaagct ctaatttgtg agtttagtat acatgcattt acttataata cagttttttta    2040
gttttgctgg ccgcatcttc tcaaatatgc ttcccagcct gcttttctgt aacgttcacc    2100
ctctacctta gcatcccttc cctttgcaaa tagtcctct ccaacaataa taatgtcaga    2160
tcctgtagag accacatcat ccacggttct atactgttga cccaatgcgt ctcccttgtc    2220
atctaaaccc acaccgggtg tcataatcaa ccaatcgtaa ccttcatctc ttccacccat    2280
gtctctttga gcaataaagc cgataacaaa atctttgtcg ctcttcgcaa tgtcaacagt    2340
acccttagta tattctccag tagataggga gcccttgcat gacaattctg ctaacatcaa    2400
aaggcctcta ggttcctttg ttacttcttc tgccgcctac ttcaaaccgc taacaatacc    2460
tgggcccacc acaccgtgtg cattcgtaat gtctgcccat tctgctattc tgtatacacc    2520
cgcagagtac tgcaatttga ctgtattacc aatgtcagca aatttctgt cttcgaagag    2580
taaaaaattg tacttggcgg ataatgcctt tagcggctta actgtgccct ccatggaaaa    2640
atcagtcaag atatccacat gtgtttttag taaacaaatt ttgggaccta atgcttcaac    2700
taactccagt aattccttgg tggtacgaac atccaatgaa gcacacaagt ttgtttgtct    2760
ttcgtgcatg atattaaata gcttggcagc aacaggacta ggatgagtag cagcacgttc    2820
cttatatgta gctttcgaca tgatttatct tcgtttcctg caggtttttg ttctgtgcag    2880
ttgggttaag aatactgggc aatttcatgt ttcttcaaca ctacatatgc gtatatatac    2940
caatctaagt ctgtgctcct tccttcgttc ttccttctgt tcggagatta ccgaatcaaa    3000
aaaatttcaa agaaaccgaa atcaaaaaaa agaataaaaa aaaaatgatg aattgaattg    3060
aaaagctagc ttatcgatga taagctgtca aagatgagaa ttaattccac ggactaataga    3120
ctatactaga tactccgtct actgtacgat acacttccgc tcaggtcctt gtcctttaac    3180
gaggccttac cactctttttg ttactctatt gatccagctc agcaaaggca gtgtgatcta    3240
agattctatc ttcgcgatgt agtaaaacta gctagaccga gaaagagact agaaatgcaa    3300
aaggcacttc tacaatggct gccatcatta ttatccgatg tgacgctgca gcttctcaat    3360
```

-continued

```
gatattcgaa tacgctttga ggagatacag cctaatatcc gacaaactgt tttacagatt  3420
tacgatcgta cttgttaccc atcattgaat tttgaacatc cgaacctggg agttttccct  3480
gaaacagata gtatatttga acctgtataa taatatatag tctagcgctt tacggaagac  3540
aatgtatgta tttcggttcc tggagaaact attgcatcta ttgcataggt aatcttgcac  3600
gtcgcatccc cggttcattt tctgcgtttc catcttgcac ttcaatagca tatctttgtt  3660
aacgaagcat ctgtgcttca ttttgtagaa caaaaatgca acgcgagagc gctaattttt  3720
caaacaaaga atctgagctg cattttttaca gaacagaaat gcaacgcgaa agcgctattt  3780
taccaacgaa gaatctgtgc ttcattttttg taaaacaaaa atgcaacgcg acgagagcgc  3840
taattttttca aacaaagaat ctgagctgca tttttacaga acagaaatgc aacgcgagag  3900
cgctatttta ccaacaaaga atctatactt cttttttttgtt ctacaaaaat gcatcccgag  3960
agcgctattt ttctaacaaa gcatcttaga ttactttttt tctcctttgt gcgctctata  4020
atgcagtctc ttgataactt tttgcactgt aggtccgtta aggttagaag aaggctactt  4080
tggtgtctat tttctcttcc ataaaaaaag cctgactcca cttcccgcgt ttactgatta  4140
ctagcgaagc tgcgggtgca tttttttcaag ataaaggcat ccccgattat attctatacc  4200
gatgtggatt gcgcatactt tgtgaacaga aagtgatagc gttgatgatt cttcattggt  4260
cagaaaatta tgaacggttt cttctatttt gtctctatat actacgtata ggaaatgttt  4320
acattttcgt attgttttcg attcactcta tgaatagttc ttactacaat ttttttgtct  4380
aaagagtaat actagagata aacataaaaa atgtagaggt cgagtttaga tgcaagttca  4440
aggagcgaaa ggtggatggg taggttatat agggatatag cacagagata tatagcaaag  4500
agatactttt gagcaatgtt tgtggaagcg gtattcgcaa tgggaagctc cacccccggtt  4560
gataatcaga aaagcccaa aaacaggaag attgtataag caaatattta aattccggaa  4620
cggcgcgcac ggattagaag ccgccgagcg ggtgacagcc ctccgaagga agactctcct  4680
ccgtgcgtcc tcgtcttcac cggtcgcgtt cctgaaacgc agatgtgcct cgcgccgcac  4740
tgctccgaac aataaagatt ctacaatact agcttttatg gttatgaaga ggaaaaattg  4800
gcagtaacct ggccccacaa accttcaaat gaacgaatca aattaacaac cataggatga  4860
taatgcgatt agttttttttag ccttatttct ggggtaatta atcagcgaag cgatgatttt  4920
tgatctatta acagatatat aaatgcaaaa actgcataac cactttaact aatactttca  4980
acattttcgg tttgtattac ttcttattca aatgtaataa aagtatcaac aaaaaattgt  5040
taatatacct ctatacttta acgtcaagga gaaaaaaccg atatcgaatt cggatccaag  5100
cttacataca aaatggaagt tgttgagagg ttctacggag agttggatgg aaaggtttcc  5160
caaggagtga acgctttgtt gggatctttc ggagttgagt tgactgatac cccaactact  5220
aagggattgc cactcgttga ttctccaact ccaattgtgt tgggagtgtc tgtttacttg  5280
accatcgtga tcggaggatt gctttggatc aaggctagag atctcaagcc aagagcttct  5340
gagccattct tgttgcaagc tttggtgttg gtgcacaact tgttctgctt cgctttgtct  5400
ctttacatgt gcgtgggtat cgcttaccaa gctatcacct ggagatattc cttgtgggga  5460
aacgcttata acccaaagca caaggagatg gctatcctcg tttacctctt ctacatgtcc  5520
aagtacgtgg agttcatgga taccgtgatc atgatcctca agagatccac cagacagatt  5580
tctttcctcc acgtgtacca ccactcttct atctccctta tctggtgggc tattgctcac  5640
cacgctccag gaggaggagc ttattggagt gctgctctca actctggagt gcacgtgttg  5700
atgtacgctt actacttctt ggctgcttgc ttgagatctt ccccaaagct caagaacaag  5760
tacctcttct ggggaagata cctcacccaa ttccagatgt tccagttcat gctcaacttg  5820
gtgcaagctt actacgatat gaaaaccaac gctccatatc cacaatggct catcaagatc  5880
ctcttctact acatgatctc cctcttgttc ctcttcggaa acttctacgt gcaaaagtac  5940
atcaagccat ccgatggaaa gcaaaaggga gctaagaccg agggtggtgg tggttctcat  6000
catcaccacc accatcatca ccatcattaa taaggtaccc cacaattgtg gggcccgggc  6060
gctagctgta caccacaatt gtggtctaga gctaagcagc tcgagcatca tcaccatcac  6120
cattaaagat ctctgcagga tatcatcatg taattagtta tgtcacgctt acattcacgc  6180
cctccccca catccgctct aaccgaaaag gaaggagtta gacaacctga agtctaggtc  6240
cctatttatt tttttatagt tatgttagta ttaagaacgt tatttatatt tcaaattttt  6300
cttttttttc tgtacaga                                                  6318
```

```
SEQ ID NO: 12        moltype = DNA   length = 5805
FEATURE              Location/Qualifiers
source               1..5805
                     mol_type = other DNA
                     note = Human
                     organism = synthetic construct
SEQUENCE: 12
cgcgtgtacg catgtaacat tatactgaaa accttgcttg agaaggtttt gggacgctcg  60
aaggctttaa tttgcaagct gcggccctgc attaatgaat cggccaacgc gcggggagag  120
gcggtttgcg tattgggcgc tcttccgctt cctcgctcac tgactcgctg cgctcggtcg  180
ttcggctgcg gcgagcggta tcagctcact caaaggcggt aatacggtta tccacagaat  240
cagggggataa cgcaggaaag aacatgtgag caaaaggcca gcaaaagccc aggaaccgta  300
aaaaggccgc gttgctggcg tttttccata ggctccgccc ccctgacgag catcacaaaa  360
atcgacgctc aagtcagagg tggcgaaacc cgacaggact ataaagatac caggcgtttc  420
cccctggaag ctccctcgtg cgctctcctg ttccgaccct gccgcttacc ggatacctgt  480
ccgcctttct cccttcggga agcgtggcgc tttctcatag ctcacgctgt aggtatctca  540
gttcggtgta ggtcgttcgc tccaagctgg gctgtgtgca cgaacccccc gttcagcccg  600
accgctgcgc cttatccggt aactatcgtc ttgagtccaa cccggtaaga cacgacttat  660
cgccactggc agcagccact ggtaacagga ttagcagagc gaggtatgta ggcggtgcta  720
cagagttctt gaagtggtgg cctaactacg gctacactag aaggacagta tttggtatct  780
gcgctctgct gaagccagtt accttcggaa aaagagttgg tagctcttga tccggcaaac  840
aaaccaccgc tggtagcggt ggtttttttg tttgcaagca gcagattacg cgcagaaaaa  900
aaggatctca agaagatcct ttgatctttt ctacgggtc tgacgctcag tggaacgaaa  960
actcacgtta agggattttg gtcatgagat tatcaaaaag gatcttcacc tagatccttt  1020
taaattaaaa atgaagtttt aaatcaatct aaagtatata tgagtaaact tggtctgaca  1080
gttaccaatg cttaatcagt gaggcaccta tctcagcgat ctgtctattt cgttcatcca  1140
tagttgcctg actccccgtc gtgtagataa ctacgatacg ggagcgctta ccatctggcc  1200
ccagtgctgc aatgataccg cgagacccac gctcaccggc tccagattta tcagcaataa  1260
```

-continued

```
accagccagc cggaagggcc gagcgcagaa gtggtcctgc aactttatcc gcctccatcc   1320
agtctattaa ttgttgccgg gaagctagag taagtagttc gccagttaat agtttgcgca   1380
acgttgttgg cattgctaca ggcatcgtgg tgtcactctc gtcgtttggt atggcttcat   1440
tcagctccgg ttcccaacga tcaaggcgag ttacatgatc ccccatgttg tgcaaaaaag   1500
cggttagctc cttcggtcct ccgatcgttg tcagaagtaa gttggccgca gtgttatcac   1560
tcatggttat ggcagcactg cataattctc ttactgtcat gccatccgta agatgctttt   1620
ctgtgactgg tgagtactca accaagtcat tctgagaata gtgtatgcgg cgaccgagtt   1680
gctcttgccc ggcgtcaata cgggataata gtgtatcaca tagcagaact ttaaaagtgc   1740
tcatcattgg aaaacgttct tcggggcgaa aactctcaag gatcttaccg ctgttgagat   1800
ccagttcgat gtaacccact cgtgcaccca actgatcttc agcatctttt actttcacca   1860
gcgtttctgg gtgagcaaaa acaggaaggc aaaatgccgc aaaaaaggga ataagggcga   1920
cacgaaatg ttgaatactc atactcttcc tttttcaatg ggtaataact gatataatta   1980
aattgaagct ctaatttgtg agtttagtat acatgcattt acttataata cagtttttta   2040
gttttgctgg ccgcatcttc tcaaatatgc ttcccagcct gcttttctgt aacgttcacc   2100
ctctacctta gcatcccttc cctttgcaaa tagtcctctt ccaacaataa taatgtcaga   2160
tcctgtagag accacatcat ccacggttct atactgttga cccaatgcgt ctcccttgtc   2220
atctaaaccc acaccgggtg tcataatcaa ccaatcgtaa ccttcatctc ttccacccat   2280
gtctctttga gcaataaagc cgataacaaa atctttgtcg ctcttcgcaa tgtcaacagt   2340
acccttagta tattctccag tagataggga gcccttgcat gacaattctg ctaacatcaa   2400
aaggcctcta ggttcctttg ttacttcttc tgccgcctgc ttcaaaccgc taacaatacc   2460
tgggcccacc acaccgtgtg cattcgtaat gtctgcccat tctgctattc tgtatacacc   2520
cgcagagtac tgcaatttga ctgtattacc aatgtcagca aattttctgt cttcgaagag   2580
taaaaaattg tacttggcgg ataatgcctt tagcggctta actgtgccct ccatggaaaa   2640
atcagtcaag atatccacat gtgtttttag taaacaaatt ttgggaccta atgcttcaac   2700
taactccagt aattccttgg tggtacgaac atccaatgaa gcacacaagt ttgtttgctt   2760
ttcgtgcatg atattaaata gcttggcagc aacaggacta ggatgagtag cagcacgttc   2820
cttatatgta gctttcgaca tgatttatct tcgtttcctg caggtttttg ttctgtgcag   2880
ttgggttaag aatactgggc aatttcatgt ttcttcaaca ctacatatgc gtatatatac   2940
caatctaagt ctgtgctcct tccttcgttc ttccttctgt tcggagatta ccgaatcaaa   3000
aaaatttcaa agaaaccgaa atcaaaaaaa agaataaaaa aaaaatgatg aattgaattg   3060
aaaagctagc ttatcgatga taagctgtca aagatgagaa ttaattccac ggactataga   3120
ctatactaga tactccgtct actgtacgat acacttccgc tcaggtcctt gtcctttaac   3180
gaggccttac cactcttttg ttactctatt gatccagctc agcaaaggca gtgtgatcta   3240
agattctatc ttcgcgatgt agtaaaacta gctagaccga gaaagagact agaaatgcaa   3300
aaggcacttc tacaatggct gccatcatta ttatccgatg tgacgctgca gcttctcaat   3360
gatattcgaa tacgctttga ggagatacag cctaatatcc gacaaactgt tttacagatt   3420
tacgatcgta cttgttaccc atcattgaat tttgaacatc cgaacctggg agttttccct   3480
gaaacagata gtatatttga acctgtataa taatatatag tctagcgctt tacggaagac   3540
aatgtatgta tttcggttcc tggagaaact attgcatcta ttgcataggt aatcttgcac   3600
gtcgcatccc cggttcattt tctgcgtttc catcttgcac ttcaatagca tatctttgtt   3660
aacgaagcat ctgtgcttca ttttgtagaa caaaaatgca acgcgagagc gctaatttt   3720
caaacaaaga atctgagctg cattttttaca gaacagaaat gcaacgcgaa agcgctattt   3780
taccaacgaa gaatctgtgc ttcatttttg taaaacaaaa atgcaacgcg acgagagcgc   3840
taattttttca aacaaagaat ctgagctgca tttttacaga acagaaatgc aacgcgagag   3900
cgctatttta ccaacaaaga atctatactt cttttttgtt ctacaaaaat gcatcccgag   3960
agcgctattt ttctaacaaa gcatcttaga ttactttttt tctcctttgt gcgctctata   4020
atgcagtctc ttgataactt tttgcactgt aggtccgtta aggttagaag aaggctactt   4080
tggtgtctat tttctcttcc ataaaaaaag cctgactcca cttcccgcgt ttactgatta   4140
ctagcgaagc tgcgggtgca ttttttcaag ataaaggcat ccccgattat attctatacc   4200
gatgtggatt gcgcatactt tgtgaacaga aagtgatagc gttgatgatt cttcattggt   4260
cagaaaatta tgaacggttt cttctatttt gtctctatat actacgtata ggaaatgttt   4320
acattttcgt attgttttcg attcactcta tgaatagttc ttactacaat ttttttgtct   4380
aaagagtaat actagagata aacataaaaa atgtagaggt cgagtttaga tgcaagttca   4440
aggagcgaaa ggtggatggg taggttatat agggatatag cacagagata tatagcaaag   4500
agatactttt gagcaatgtt gtgtggaagc g gtattcgcaa tgggaagctc caccccggtt   4560
gataatgaaa aaagccccaa aaacaggaag attgtataag caaatatttta aattccggaa   4620
cggcgcgcac ggattagaag ccgccgagcg ggtgacagcc ctccgaagga agactctcct   4680
ccgtgcgtcc tcgtcttcac cggtcgcgtt cctgaaacgc agatgtgcct cgcgccgcac   4740
tgctccgaac aataaagatt ctacaatact agctttatg gttatgaaga ggaaaaattg   4800
gcagtaacct ggccccacaa accttcaaat gaacgaatca aattaacaac cataggatga   4860
taatgcgatt agtttttttag ccttatttct ggggtaatta atcagcgaag cgatgatttt   4920
tgatctatta acagatatat aaatgcaaaa actgcataac cactttaact aatactttca   4980
acattttcgg tttgtattac ttcttattca aatgtaataa aagtatcaac aaaaaattgt   5040
taatatacct ctatacttta acgtcaagga gaaaaaaccg atatcgaatt cggatccaag   5100
cttacataca aaatgggaat ccaaggaggg tctgtcctgt tcgggctgct gctcgtcctg   5160
gctgtcttct gccattcagg tcatagccat caccatcacc atcacctgca gtgctacaac   5220
tgtcctaacc caactgctga ctgcaaaaca gccgtcaatt gttcatctga ttttgatgcc   5280
tgtctcatta ccaaagctgg gttacaagtg tataacaagt gttggaagtt tgagcattgc   5340
aatttcaacg acgtcacaac ccgcttgagg gaaaatgagc taacgtacta ctgctgcaag   5400
aaggacctgt gtaactttaa cgaacagctt gaaatggtg ggacatcctt atcagagaaa   5460
acagttcttc tgctggtgac tccatttctg gcagcagcct ggagccttca tccctaataa   5520
ggtacccac aattgtgggg cccgggcgct agctgtacac gacaatttgtg gtctagagct   5580
aagcagctcg agcatcatca ccatcaccat taaagatctc tgcaggatat catcatgtaa   5640
ttagttatgt cacgcttaca ttcacgccct ccccccacat ccgctctaac cgaaaaggaa   5700
ggagttagac aacctgaagt ctaggtccct atttattttt ttatagttat gttagtatta   5760
agaacgttat ttatatttca aatttttctt tttttctgt acaga               5805
```